(12) United States Patent
Mohajerzadeh et al.

(10) Patent No.: US 8,956,820 B2
(45) Date of Patent: Feb. 17, 2015

(54) METHOD FOR DETECTING CANCER CELLS USING VERTICALLY ALIGNED CARBON NANOTUBES

(76) Inventors: Shamsoddin Mohajerzadeh, Tehran (IR); Mohammad Abdolahad, Tehran (IR); Zeinab Sanaee, Tehran (IR); Mohammad Abdollahi, Tehran (IR)

(*) Notice: Subject to any disclaimer, the term of this patent is extended or adjusted under 35 U.S.C. 154(b) by 13 days.

(21) Appl. No.: 13/450,720

(22) Filed: Apr. 19, 2012

(65) Prior Publication Data
US 2013/0102027 A1 Apr. 25, 2013

Related U.S. Application Data

(60) Provisional application No. 61/476,771, filed on Apr. 19, 2011.

(51) Int. Cl.
| | | |
|---|---|---|
| *C12Q 1/04* | (2006.01) | |
| *G01N 33/574* | (2006.01) | |
| *C12N 5/09* | (2010.01) | |
| *G01N 19/08* | (2006.01) | |
| *G01N 23/225* | (2006.01) | |
| *B82Y 5/00* | (2011.01) | |
| *B82Y 15/00* | (2011.01) | |
| *H01J 37/20* | (2006.01) | |
| *H01J 37/28* | (2006.01) | |

(52) U.S. Cl.
CPC ............ *G01N 19/08* (2013.01); *G01N 23/2251* (2013.01); *C12N 5/0693* (2013.01); *B82Y 5/00* (2013.01); *B82Y 15/00* (2013.01); *H01J 37/20* (2013.01); *G01N 2203/0089* (2013.01); *G01N 2223/6126* (2013.01); *H01J 37/28* (2013.01)
USPC .......... 435/6.14; 435/7.23; 435/366; 435/369

(58) Field of Classification Search
USPC .................................................. 435/405.5
See application file for complete search history.

(56) References Cited

U.S. PATENT DOCUMENTS

| 8,372,579 B2* | 2/2013 | Toner et al. ...................... 435/2 |
| 2007/0026415 A1* | 2/2007 | Fuchs et al. ...................... 435/6 |
| 2007/0059680 A1* | 3/2007 | Kapur et al. ..................... 435/4 |
| 2010/0227382 A1* | 9/2010 | Lieber et al. ............... 435/287.1 |
| 2010/0233694 A1* | 9/2010 | Kopf-Sill .......................... 435/6 |

OTHER PUBLICATIONS

Cross, AFM-based analysis of human metastatic cancer cells, Nanotechnology, vol. 19 2008.*
Tan, Cells lying on a bed of micro-needles, PNAS, 2003, vol. 100, No. 4.*
Kim, Carbon Nanotubes for Electronic and Electrochemical detection of biomolecules, Advanced Materials, 2007, vol. 19, 3214-3228.*
Li, Biomolecular sensing for cancer diagnostics using carbon nanotubes, BioMEMS and Biomed. Nanotech., vol. 1, 2006.*
Sinha, Carbon nanotubes for biomedical applications, IEEE Trans. of NanoBioSci. vol. 4, No. 2 , Jun. 2005.*
Suresh, Biomechanics and biophysics of cancer cells, Acta Biomaterials, 2007, 3(4): 413-438.*

\* cited by examiner

*Primary Examiner* — Taeyoon Kim
*Assistant Examiner* — Srikanth Patury
(74) *Attorney, Agent, or Firm* — Barry Choobin; Patent 360 LLC

(57) ABSTRACT

The various embodiments herein provide a method for detecting the cancerous cells using the carbon nanotubes. The method comprises preparing a solution of the tissue cells. The prepared solution of the tissue cells is poured on a fabricated substrate to carry out an entrapment of the tissue cells on the substrate. The substrate is dried after the entrapment in an air ambient and observed under a scanning electron microscope. The cancer cell is detected based on the biomechanical properties such as softness, deformability and an elasticity of the cancer cells. The cancer cell is detected based on the deflection of the substrate due to the entrapment of the cancer cells.

9 Claims, 38 Drawing Sheets

METHOD FOR DETECTING CANCER CELLS USING VERTICALLY ALIGNED CARBON NANOTUBES

CROSS-REFERENCE TO RELATED APPLICATION

This application claims the priority under 35 USC 119(e) of U.S. Provisional Application Ser. No. 61/476,771 filed Apr. 19, 2011 which is included by reference herein.

BACKGROUND

1. Technical Field

The embodiments herein generally relate to a method for detecting the cancer cells in the tissues. The embodiments herein particularly relate to a method of detecting the cancer cells using the bio-mechanical properties of the individual human cells. The embodiments herein particularly relate to a method of detecting the cancer cells in the biological tissues based on a deflection of the vertically aligned carbon nanotubes due to the deformability of the cancer cells.

2. Description of the Related Art

Although the biological cells lack eyes and ears to see and hear but they seem to have a sense of touch that allows them to feel their microenvironment. It is now well accepted that the cellular functions are essentially determined by their structure. The structural organization of cells is characterized by certain mechanical properties at different hierarchy levels. The elasticity and the responses of living cells to the external forces have attracted tremendous attention in the modern research of tissue engineering as well as in cell biology and cancer investigations. The living cells respond to the mechanical stimuli in their native environments with the biological changes such as a shape alteration of the membranes and nuclei, a cell-spreading, actins and microtubule reorganization or a cross-linking under a cell membrane and a cell bursting or motility. One can obtain an important information on a tumoral stage of the cancerous cells by investigating these responses. The screening of the cells based on their biomechanical properties provides a powerful tool for a label-free diagnosis and staging of the cancers through the variation of their mechanical properties such as elasticity.

It is well known that a wide range of changes occur during the cancerous transformation of a normal cell. All the cancer cells acquire an ability to grow and divide in the absence of the appropriate signals and/or in the presence of the inhibitory signals. There are also detectable changes in the physical properties of the cells. These changes are classified as cytoskeletal changes, a cell adhesion, motility, nuclei changes and an enzyme production. The latter two cases refer to the variation of the cells from inside where the shape and the organization of the nuclei of cancer cells are markedly different from that of the normal cells of the same origin or special enzymes are secreted to invade the neighboring cells. However, in the cytoskeletal changes, the distribution and activity of the microfilaments and the microtubules may change. These alterations change the way in which the cell interacts with the neighboring cells and alter the appearance of the cells. The changes in the cytoskeleton also affect the cell adhesion and a cell movement or motility. In general the cancer cells are more deformable than the normal cells. Lastly the cancer cells exhibit a remarkable reduction in their cell-to-cell and cell-to-extracellular matrix adhesion which allows a formation of large masses in the cells. The alterations in the cell adhesion property also have an impact on the ability of the cells to move. The cancer cells spread over an area due to their ability to move and migrate. The cell adhesion plays a major role in regulating the cell movement. Two of these main changes i.e. cytoskeletal and cell adhesion are directly related to the mechanical properties of the cells.

During the development of the diseases such as cancer, the structures of the cytoskeleton and the extracellular matrix are often transformed. With the cell progressing from a fully mature, post mitotic state to a cancerous state, the cytoskeleton experiences a reduction in the amount of constituent polymers and accessory proteins resulting in a restructuring of its bio-polymeric network. Therefore a direct correlation seems to exist between an increase in the deformability and a progression from a non-tumoral cell to a tumoral and metastatic one. The altered cytoskeleton enhances the ability of cancer cells to contract or stretch. As a result the tumor cells exhibit a lower resistance to a deformation in comparison with the normal cells even when they are more deformable than the non-metastatic cells. On the other hand the micro and nano-fabrication technology developments have profound contributions to a cancer detection by measuring the changes in the mechanical properties of the cancerous transformed cells at their early stages.

Many methods are employed to investigate the mechanical properties of the bio-cells in living, dead and fixed forms. For example, the biophysical tools and techniques such as an atomic force microscopy, a micropipette aspiration, Micro Post Array Detectors (MPAD) and the optical stretcher, are used to probe the mechanical properties of the different types of the cells. In addition to the above, several models are developed to study the mechanical properties of these cells. The properties of the several kinds of the benign and malignant cells such as the breast cancer cells and the other types of cells are studied.

On the other hand, the carbon nanotubes are known to possess remarkable electrical, mechanical and biological properties. Their unique fluorescent specifications and the possible applications in bio-sensing and cancer therapy are discussed by many researchers. It has been shown that various cell types engulf carbon nano tubes (CNT), suggesting their potential usage as the delivery vehicles for a biologically active cargo. They are also used as a cell culture media. These applications, however, rely upon a nonspecific interaction between the CNTs and the cell surfaces, which precludes targeting to a particular cell-type within a mixed population or to a specific organelle within a cell.

The biological applications of the vertical Multi Wall Carbon Nano-Tube (MWCNT) arrays on an interaction with micro organism and biological cells have been investigated. But none of the papers provide the use of carbon nanotubes for the detection of the various types of cancer cells.

Hence there is a need to develop a method to detect the various types and stages of cancer cells using the deflection of the carbon nanotubes and the entrapment of the cancer cells in the carbon nanotubes.

The above mentioned shortcomings, disadvantages and problems are addressed herein and which will be understood by reading and studying the following specification.

OBJECTIVES OF THE EMBODIMENTS HEREIN

The primary object of the embodiments herein is to provide a method to detect the presence of cancer cells using the biomechanical properties of the cancer cells.

Another object of the embodiments herein is to provide a method to detect the cancer cells utilizing the vertically aligned multiwall carbon nanotubes.

Yet another object of the embodiments herein is to provide a method to determine the various types of cancer cells.

Yet another object of the embodiments herein is to provide a method to detect the cancer cells based on a deflection of the vertically aligned multiwall CNTs due to a stress applied by the cancerous cells.

Yet another object of the embodiments herein is to provide a method to detect the cancer cells based on a considerable amount of deflection of the vertically aligned multiwall CNTs due to an anomalous entrapment of the cancerous cells.

Yet another object of the embodiments herein is to provide a method of detecting the various types of cancer cells such as colon cancer cells, renal or kidney carcinoma cells and brain tumoral cells like astrocytoma tumor cells.

Yet another object of the embodiments herein is to provide a method to distinguish the cancer cells from the normal healthy cells based on the biomechanical properties and the selective entrapment of the cancer cells in the vertically aligned multiwall carbon nanotubes.

Yet another object of the embodiments herein is to provide a method of detecting the cancer cells based on an entrapment of the cancer cells on the CNT arrays to test the new medicines and their effects on the mechanical properties of the cells as a vital monitoring signal in a laboratory.

These and other objects and advantages of the embodiments herein will become readily apparent from the following detailed description taken in conjunction with the accompanying drawings.

SUMMARY

The various embodiments herein provide a method for detecting cancerous cells using the vertically aligned multiwall carbon nanotube arrays. According to one embodiment herein, a method of detecting cancer cells using carbon nanotubes comprises preparing a first solution of a plurality of tissue cells. A substrate is fabricated. The substrate is an array of carbon nanotubes. The carbon nanotubes are a vertically aligned Multiwall Carbon Nanotubes (MWCNTs). Further the substrate is irradiated. A first solution of the plurality of tissue cells is poured on the substrate after an irradiation. An entrapment of the plurality of tissue cells is allowed on the substrate. The substrate is dried in an air environment after the entrapment of the plurality of tissue cells. The substrate is observed in a scanning electron microscope after a drying step.

A plurality of cancer cells are detected based on biomechanical properties of the plurality of cancer cells. The biomechanical properties of the plurality of cancer cells includes a softness of the plurality of cancer cells, a deformability of the plurality of cancer cells, an elasticity of the plurality of cancer cells and an entrapment of the plurality of cancer cells. The plurality of cancer cells are detected by observing a deflection of the substrate due to an entrapment of the plurality of cancer cells on the substrate.

The plurality of cancer cells is selected from a group consisting of a cancer cells from colon, a cancer cells from kidney and a cancer cells from brain. The plurality of tissue cells is selected from a group consisting of cells taken from a colon, cells taken from a kidney and cells taken from a brain.

The substrate is fabricated using a direct-current plasma enhanced chemical vapor deposition technique. The substrate is held at an angle of 45 degrees. The first solution of the plurality of tissue cells is poured on the substrate using a peristaltic pump. The first solution of the plurality of tissue cells is poured on the substrate at a preset flow rate. The preset flow rate is within a range of 2.5 cc/min to 20 cc/min. The scanning electron microscope is used to detect a deflection of the substrate due to an entrapment of the plurality of cancer cells on the substrate.

The method of detecting cancer cells using carbon nanotubes is based on a difference in a fraction of entrapped cells on the substrate. The difference in a fraction of the entrapped cells on the substrate depends on a type of the plurality of cancer cells. The difference in a fraction of the entrapped cells on the substrate depends on a metastatic stage of the plurality of cancer cells.

The plurality of cancer cells are detected based on a deflection angle of the carbon nanotubes. The deflection angle of the carbon nanotubes depends on a softness and deformability of the plurality of cancer cells. The plurality of the cancer cells are detected based on a comparison of a softness of the plurality of cancer cells with a softness of a plurality of healthy cells. The softness of the plurality of cancer cells is more than the softness of a plurality of healthy cells. The deflection caused by the plurality of cancer cells on the substrate depends on a deformability and elasticity of the plurality of cancer cells. The plurality of cancer cells is detected by comparing a deformability and elasticity of the plurality of cancer cells to a deformability and elasticity of the plurality of healthy cells. The deformability and elasticity of the plurality of cancer cells on the substrate is more than the deformability and elasticity of the plurality of healthy cells. The deflection angle of the substrate depends on a type of the tissue cells. The entrapment of the tissue cells applies a shear force on the substrate. The shear force applied by the plurality of cancer cells is 0.3 nN. The shear force applied by a plurality of healthy cells is 0.022 nN.

According to one embodiment herein, a method of detecting cancer in a human body comprises the steps of first preparing a solution of cancerous cells. Then, fabricating a substrate and pouring the prepared solution of cancerous cells on the fabricated substrate to form a prepared substrate. Drying the prepared substrate in an ambient air environment and observing the dried substrate under scanning electron microscope to detect the cancerous cells. The substrate is fabricated using a chemical vapour deposition technique. The substrate is an array of vertically aligned multiwall carbon nanotubes. The cancer cells are selected from a group consisting of cancer cells from colon, cancer cells from kidney and cancer cells from brain. The prepared solution is poured on the substrate held at an angle of 45 degrees by using a peristaltic pump. The prepared solution is poured at a flow rate of 2.5 cc/min to 20 cc/min. The dried substrate is observed for any deflection caused by the cancer cells on the substrate.

According to another embodiment herein, a method is provided to differentiate between a cancerous cell and a healthy cell. The differentiation is done on a basis that the cancerous cells are more contracted on the substrate as compared to the healthy cell.

According to another embodiment herein, the method is provided to determine a metastatic stage of a cancerous cell.

According to another embodiment herein, a system is provided to detect presence of cancer cells. The system further comprises a substrate, a peristaltic pump, a drier and a scanning electron microscope. The substrate includes an array of multiwall carbon nanotubes (MWCNTs). The MWCNTs are vertically aligned. The substrate has a surface area of $0.5 \text{ cm}^2$. The peristaltic pump has a diameter of 0.8 cm. The peristaltic pump transfers a solution at a flow rate of 2.5 cc/min to 20 cc/min. The substrate is tilted at an angle of 45 degrees. The scanning electron microscope is used to detect a deflection caused by an entrapment of cancerous cells on the substrate.

These and other aspects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF THE DRAWINGS

The other objects, features and advantages will occur to those skilled in the art from the following description of the preferred embodiment and the accompanying drawings in which.

Figure 1:
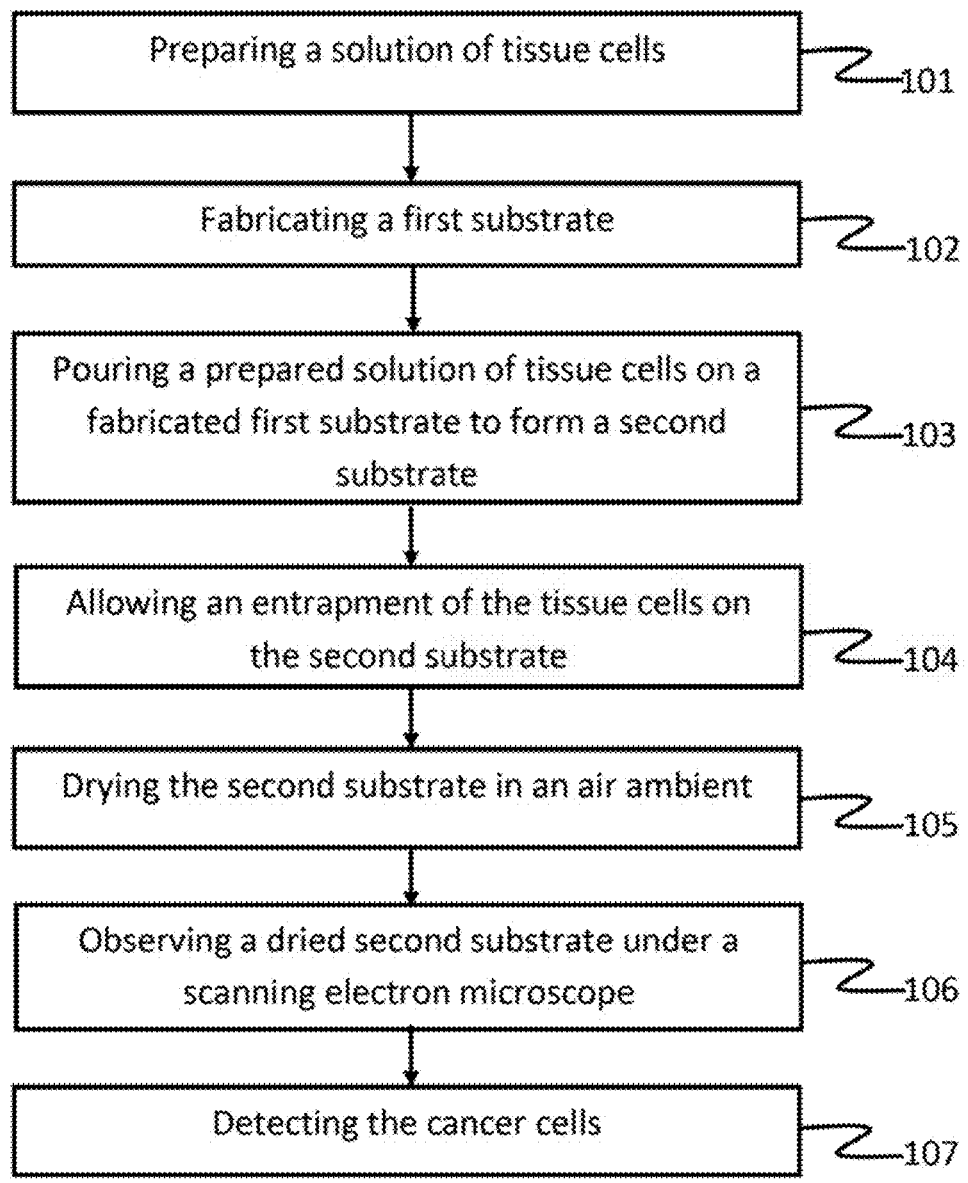
FIG. 1 shows a flowchart illustrating the various steps involved in a method of detecting cancerous cells using carbon nanotubes (CNTs), according to an embodiment herein.

Although the specific features of the embodiments herein are shown in some drawings and not in others. This is done for convenience only as each feature may be combined with any or all of the other features in accordance with the embodiments herein.

DETAILED DESCRIPTION OF THE EMBODIMENTS

In the following detailed description, a reference is made to the accompanying drawings that form a part hereof, and in which the specific embodiments that may be practiced is shown by way of illustration. The embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments herein provide a method for detecting cancerous cells using the vertically aligned multi-wall carbon nanotube arrays. According to one embodiment herein, a method of detecting cancer cells using carbon nanotubes comprises preparing a first solution of a plurality of tissue cells. A substrate is fabricated. The substrate is an array of carbon nanotubes. The carbon nanotubes are a vertically aligned Multiwall Carbon Nanotubes (MWCNTs). Further the substrate is irradiated. A first solution of the plurality of tissue cells is poured on the substrate after an irradiation. An entrapment of the plurality of tissue cells is allowed on the substrate. The substrate is dried in an air environment after the entrapment of the plurality of tissue cells. The substrate is observed in a scanning electron microscope after a drying step.

A plurality of cancer cells are detected based on biomechanical properties of the plurality of cancer cells. The biomechanical properties of the plurality of cancer cells includes a softness of the plurality of cancer cells, a deformability of the plurality of cancer cells, an elasticity of the plurality of cancer cells and an entrapment of the plurality of cancer cells. The plurality of cancer cells are detected by observing a deflection of the substrate due to an entrapment of the plurality of cancer cells on the substrate.

The plurality of cancer cells is selected from a group consisting of a cancer cells from colon, a cancer cells from kidney and a cancer cells from brain. The plurality of tissue cells is selected from a group consisting of cells taken from a colon, cells taken from a kidney and cells taken from a brain.

The substrate is fabricated using a direct-current plasma enhanced chemical vapor deposition technique. The substrate is held at an angle of 45 degrees. The first solution of the plurality of tissue cells is poured on the substrate using a peristaltic pump. The first solution of the plurality of tissue cells is poured on the substrate at a preset flow rate. The preset flow rate is within a range of 2.5 cc/min to 20 cc/min. The scanning electron microscope is used to detect a deflection of the substrate due to an entrapment of the plurality of cancer cells on the substrate.

The method of detecting cancer cells using carbon nanotubes is based on a difference in a fraction of entrapped cells on the substrate. The difference in a fraction of the entrapped cells on the substrate depends on a type of the plurality of cancer cells. The difference in a fraction of the entrapped cells on the substrate depends on a metastatic stage of the plurality of cancer cells.

The plurality of cancer cells are detected based on a deflection angle of the carbon nanotubes. The deflection angle of the carbon nanotubes depends on a softness and deformability of the plurality of cancer cells. The plurality of the cancer cells are detected based on a comparison of a softness of the plurality of cancer cells with a softness of a plurality of healthy cells. The softness of the plurality of cancer cells is more than the softness of a plurality of healthy cells. The deflection caused by the plurality of cancer cells on the substrate depends on a deformability and elasticity of the plurality of cancer cells. The plurality of cancer cells is detected by comparing a deformability and elasticity of the plurality of cancer cells to a deformability and elasticity of the plurality of healthy cells. The deformability and elasticity of the plurality of cancer cells on the substrate is more than the deformability and elasticity of the plurality of healthy cells. The deflection angle of the substrate depends on a type of the tissue cells. The entrapment of the tissue cells applies a shear force on the substrate. The shear force applied by the plurality of cancer cells is 0.3 nN. The shear force applied by a plurality of healthy cells is 0.022 nN.

According to one embodiment herein, a method of detecting cancer in a human body comprises the steps of first preparing a solution of cancerous cells. Then, fabricating a substrate and pouring the prepared solution of cancerous cells on the fabricated substrate to form a prepared substrate. Drying the prepared substrate in an ambient air environment and observing the dried substrate under scanning electron microscope to detect the cancerous cells. The substrate is fabricated using a chemical vapour deposition technique. The substrate is an array of vertically aligned multiwall carbon nanotubes. The cancer cells are selected from a group consisting of cancer cells from colon, cancer cells from kidney and cancer cells from brain. The prepared solution is poured on the substrate held at an angle of 45 degrees by using a peristaltic pump. The prepared solution is poured at a flow rate of 2.5 cc/min to 20 cc/min. The dried substrate is observed for any deflection caused by the cancer cells on the substrate.

According to another embodiment herein, a method is provided to differentiate between a cancerous cell and a healthy cell. The differentiation is done on a basis that the cancerous cells are more contracted on the substrate as compared to the healthy cell.

According to another embodiment herein, the method is provided to determine a metastatic stage of a cancerous cell.

According to another embodiment herein, a system is provided to detect presence of cancer cells. The system further comprises a substrate, a peristaltic pump, a drier and a scanning electron microscope. The substrate includes an array of multiwall carbon nanotubes (MWCNTs). The MWCNTs are vertically aligned. The substrate has a surface area of 0.5 cm². The peristaltic pump has a diameter of 0.8 cm. The peristaltic pump transfers a solution at a flow rate of 2.5 cc/min to 20 cc/min. The substrate is tilted at an angle of 45 degrees. The scanning electron microscope is used to detect a deflection caused by an entrapment of cancerous cells on the substrate.

According to an embodiment herein, the Multi Wall Carbon Nanotubes (MWCNTs) are utilized to detect a presence of the cancerous cells. The vertically aligned MWCNTs are used as suitable candidates for a cancer cell diagnosis. The detection is based on the differences in the fraction of the entrapped cells on the CNT arrays which depends on a type and a metastatic stage of the cancerous cells. The entrapment of the cancer cells results in the deflection of the CNT beam. The deflection angle of CNT beam depends on the softness and a deformability of the cancer cells and the type of a tissue.

The selective entrapment of the cancer cells on the vertically aligned MWCNT arrays depend on the deformability of the cells and the elasticity of the cells in comparison with that of the healthy ones. This is a novel method to detect the cancerous transformation of the cells. The higher metastatic transformation of the cancer cells results in an observable increase in the cell entrapment on the CNT arrays which is believed to be due to a more deformable structure of the higher metastatic cancer cells (HT 29 and SW 48 live cells). A fixation of the cancer cells results in a sharp decrease in the entrapment of the cells on the CNT arrays because of the more rigid structure of fixed cells. A thermal irradiation of the CNT surface before pumping the cell solution favorably affects the fraction of the entrapped cells. A rise in the flow rate of the cell solution pumping onto the CNT arrays results in a drop of the cell entrapment. An increase in a solution pumping flow rate from 2.5 cc/min to 20 cc/min results in a decrease in the fraction of cell entrapment by a factor of 15 (from 75% to 5%).

The entrapment mechanism of the cancer cells on the CNT arrays are investigated for both the cell line samples (colon cancer cells with two different stages of metastasis) and the clinical cells from the known cases of a surgery (renal carcinoma and astrocytoma). The healthy cells have rigid and non-deformable structures in comparison with the cancer ones. No entrapment of the fixed healthy renal cells occurs on the CNT arrays but an entrapment of the fixed renal cancer cells clearly occurs on the CNT arrays. A shear force applied by the entrapped cells on the carbon nanotube beams is 0.3 nN as opposed to a shear force of 0.022 nN applied by the healthy glomerular cells. The Astrocytoma cells get entrapped on the CNT arrays and deflect the nanotube beams in lower angles. This is due to the softness of the brain tissues and the shape of the astrocytoma cells.

The cancer cells are highly contracted on the CNTs while the healthy ones are not affected. Also the transformation of the cancer cells to a higher metastatic stage results in an increment of their entrapment on the CNT arrays.

According to an embodiment herein, a method is provided to detect a cancer in the brain cells, colon cells and kidney cells.

FIG. 1 shows the flowchart illustrating the various steps involved in a method of detecting cancerous cells using carbon nanotubes (CNTs), according to an embodiment herein. With respect to FIG. 1, a solution of tissue cells is prepared (101). A first substrate is fabricated (102). The prepared solution of tissue cells is poured on the fabricated first substrate to form a second substrate (103). An entrapment of the tissue cells on the second substrate is carried out (104). The second substrate is dried in an air ambient (105). The dried second substrate is observed under a scanning electron microscope (106). The cancer cells are detected (107). The cancer cells include the cancer cells from a colon or the cancer cells from a kidney or the cancer cells from the brain. The tissue cells include the cells taken from a colon or a kidney or a brain. The first substrate is fabricated using a chemical vapour deposition technique. The prepared solution of the tissue cells is poured on the second substrate using a peristaltic pump. The second substrate is held at an angle of 45 degrees. The prepared solution of the tissue cells is poured at a flow rate of 2.5 cc/min to 20 cc/min.

According to an embodiment herein, the cancer cells are selected from a group consisting of the cancer cells from a colon, the cancer cells from a kidney and the cancer cells from the brain. The substrate is an array of the vertically aligned multiwall carbon nanotubes. The prepared solution is poured using a peristaltic pump on a substrate held at an angle of 45 degrees. The prepared solution is poured at a flow rate of 2.5 cc/min to 20 cc/min. The dried substrate is observed for any deflection caused by the cancer cells on the substrate. The method is used to differentiate a cancerous cell from a healthy cell. The differentiation is done based on the principle that the cancerous cell is highly contracted on the substrate as compared to the healthy cell. The method is used to determine a metastatic stage of a cancerous cell.

Experimental Data

Two different metastasis stages of the colon cancer cells were prepared in a cell culture. For a clinical test, a known renal cancer case as used. The cells were removed from the known renal cancer case by means of nephrectomy. The astrocytoma tumor cells were removed by a tumor excision method. It was observed that the cancer cells are highly contracted on the CNTs as compared to the healthy ones which remain rigid and unaffected. Also a transformation of the cancer cells to a higher metastatic stage results in an increment of their entrapment on the CNT arrays due to a more deformed and softer structure.

Cell Preparation

Colon Cell Culture: Two cell lines were obtained from the National Cell Bank of Iran, Pasteur Institute. The HT29 and SW 48 cell lines were isolated from grade I and IV Human colon tumors. The cells were maintained at 37° C. in the presence of 5% $CO_2$ and 95% air in RPMI-1640 medium (Sigma 8758) supplemented with 5% fetal bovine serum (Gibco), and 1% penicillin/streptomycin (Gibco). The fresh medium was replaced every day. The HT29 cells were harvested with 0.25% trypsin EDTA solution (Invitrogen) and the suspended cells with augmented medium were exposed on the CNT arrays.

Renal Cell preparation: After removing the normal and tumoral tissue from a known renal carcinoma case by nephrectomy, the removed living tissues were immediately fixed by a 10% formaldehyde solution. The cell separation process starts by slicing both the normal and tumoral tissue followed by an ultrasonic bath agitation for about 10 hours. The next sequence was centrifuging the solutions at a rate of 2500 rpm for 5 min. Finally a part of each cancerous and benign cell solutions was dropped on a microscope slide by the individual samplers and a papanicolaous-staining method was applied on the samples. The stained samples were imaged by an optical microscopy to ensure that the cells were completely separated.

Brain cancer cell preparation: The brain tumoral cells were removed from a known case of astrocytoma by a tumor excision process. Then the cells were fixed by a 10% formaldehyde solution. The cells solution was held in an ultrasonic bath for about 4 hours for a separation of the cells from the solid tissue. Because of the softness of the brain tissue, the time of brain tissue cell separation is shorter than that of the renal tissues. Finally the same papanicolaous-staining method was applied on the brain samples. The stained samples were imaged by an optical microscopy to ensure that the cells were completely separated.

Fabrication of MWCNT: A growth of the MWCNT arrays was achieved using a direct-current plasma enhanced chemical vapor deposition technique. A mixture of $H_2$ and $C_2H_2$ gases at a pressure of 1-5 ton and at a temperature of 550° C. and a plasma power density of 5 W/cm$^2$ were typically employed. A hydrogenation step was needed prior to the growth of CNTs to form the nano-size islands of nickel which act as a catalyst layer for the growth of CNTs.

Ex Vitro test of Cells entrapped by CNT: In order to conduct the individual tests on the CNT-holding substrates, the separated solution of benign and malignant cells were poured onto the target substrate surface, held by an angle of 45°, by a peristaltic pump acquired from Watson-Marlow Bredel Pumps Co.) Model 323E/D). The diameter of the tube of the pump, which transfers the solution, was 0.8 cm and the cell solutions were pumped with different flow rates ranging from 2.5 cc/min to 20 cc/min. The cell solutions were poured with different flow rates to trigger an acceleration of the cells during a movement on the surface of the CNT arrays. The optimum acceleration of the cells on the CNT arrays was estimated to be more than 7 m/sec$^2$ for a flow rate of 20 cc/min. The volume of cell solution was about 0.5 mL and the surface of the target substrate was about 0.5 cm$^2$. After pouring the cells onto the CNT arrays, they were dried in an air ambient. A Hitachi make field emission scanning electron microscope has been extensively used to study the prepared specimens.

The HT29 and SW 48 cell lines which are stage 1 and 4 metastasis of colon cancer cells respectively were obtained from the National Cell Bank of Iran, Pasteur Institute and the resulted suspended cells with augmented medium were exposed to the CNT arrays. For a Renal Cell preparation, the normal and tumoral tissues were removed from a known renal carcinoma case by nephrectomy and the removed living tissues were immediately fixed by a 10% formaldehyde solution. The cell separation process was applied on both the healthy and cancerous tissues, and a papanicolaous-staining method was applied on the samples. The stained samples were imaged by an optical microscopy to ensure that the cells were completely separated. Finally, the brain cancer cells were prepared from the brain tumoral cells, which were removed from a known case of astrocytoma by a tumor excision process. In this case, the fixation and the cell separation process were applied in a method which is slightly different from the method for the renal cells. The stained samples were imaged by an optical microscopy to ensure that the cells were completely separated.

Figure 2A:
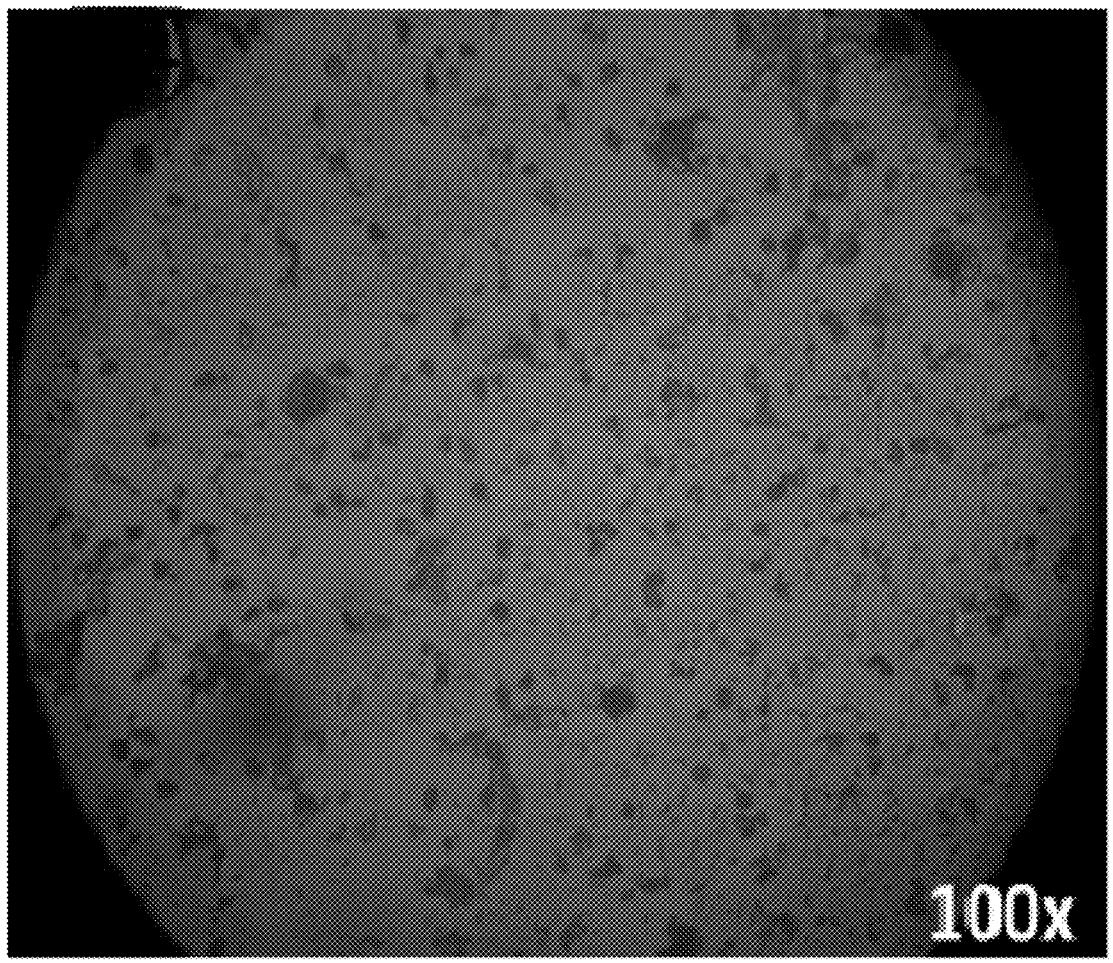
FIG. 2A shows an optical microscopy image of separated and fixed renal healthy cells stained by a papanicolaous-staining method with a magnification factor of 100×, according to an embodiment herein.
Figure 2B:
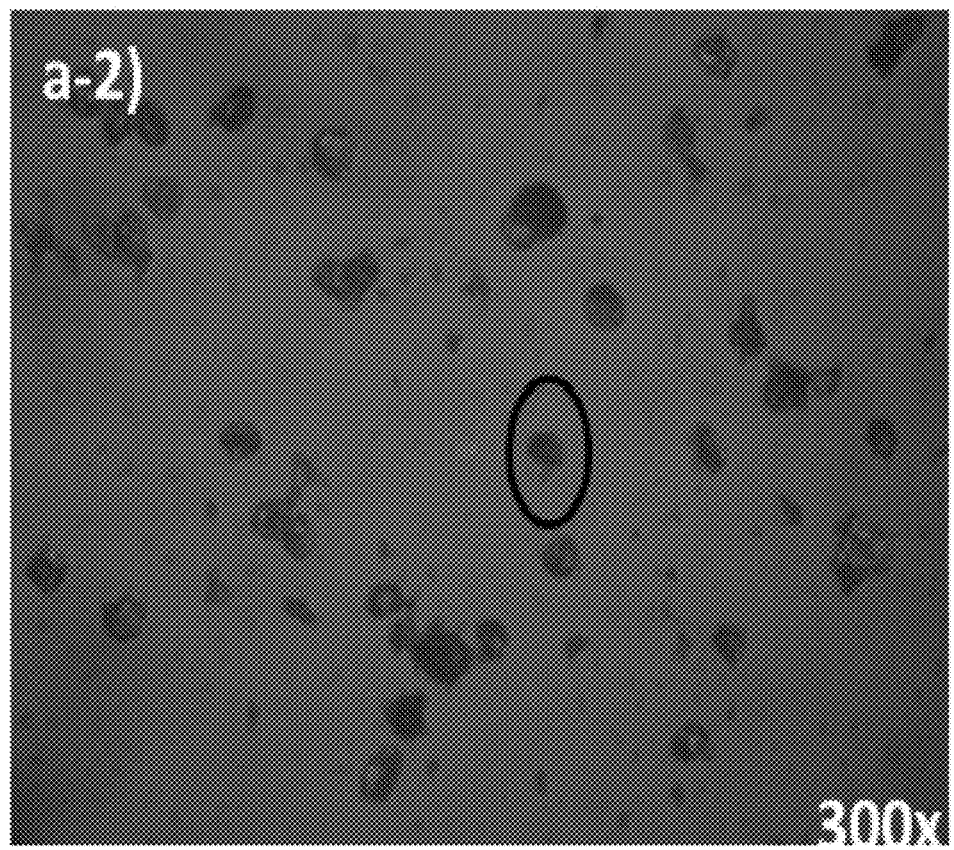
FIG. 2B shows an optical microscopy image of separated and fixed renal healthy cells stained by a papanicolaous-staining method with a magnification factor of 300×, according to an embodiment herein.
Figure 2C:
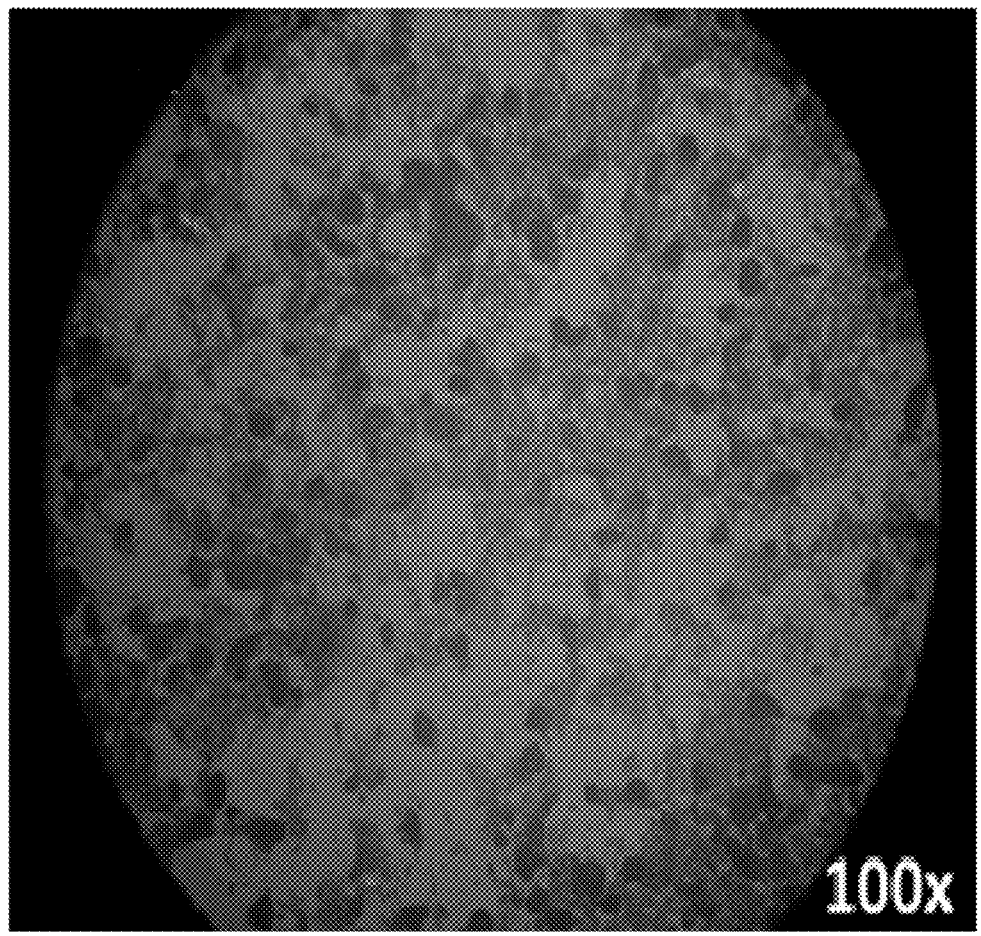
FIG. 2C shows an optical microscopy image of separated and fixed renal cancer (renal carcinoma) cells stained by a papanicolaous-staining method with a magnification factor of 100×, according to an embodiment herein.
Figure 2D:
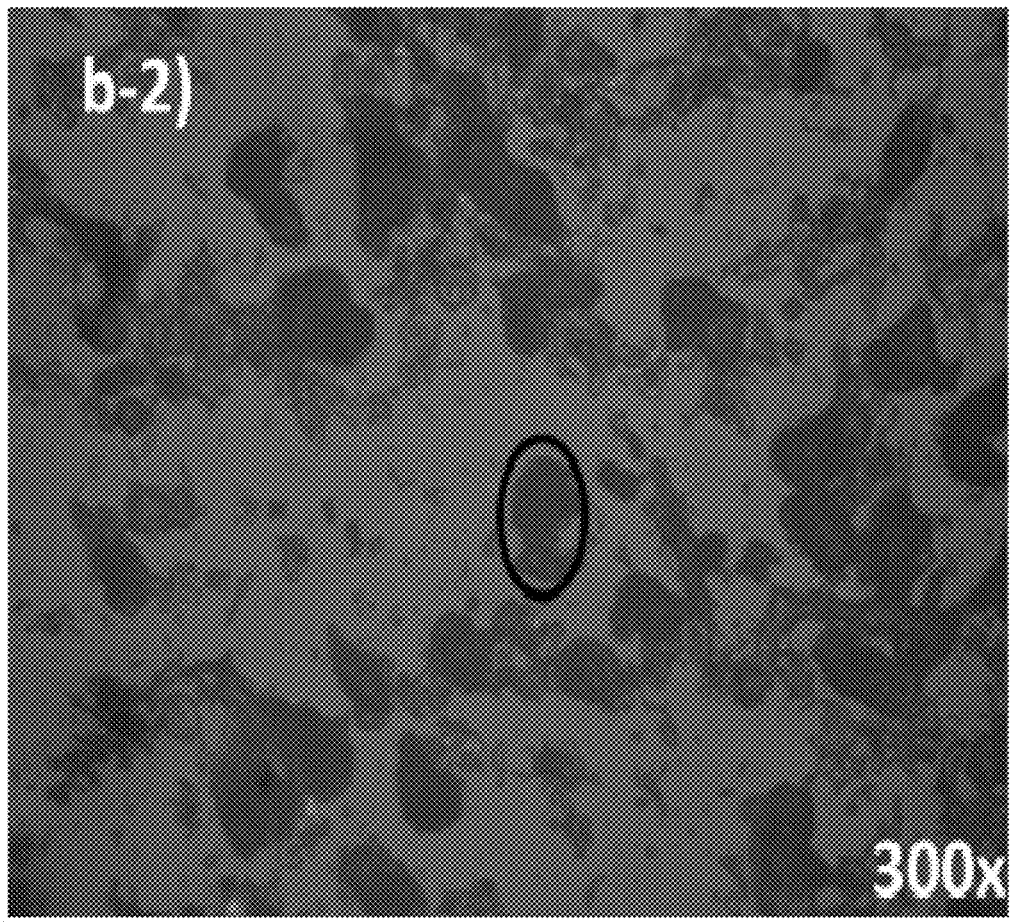
FIG. 2D shows an optical microscopy image of renal cancer or renal carcinoma cells stained by a papanicolaous-staining method with a magnification factor of 300×, according to an embodiment herein.
Figure 2E:
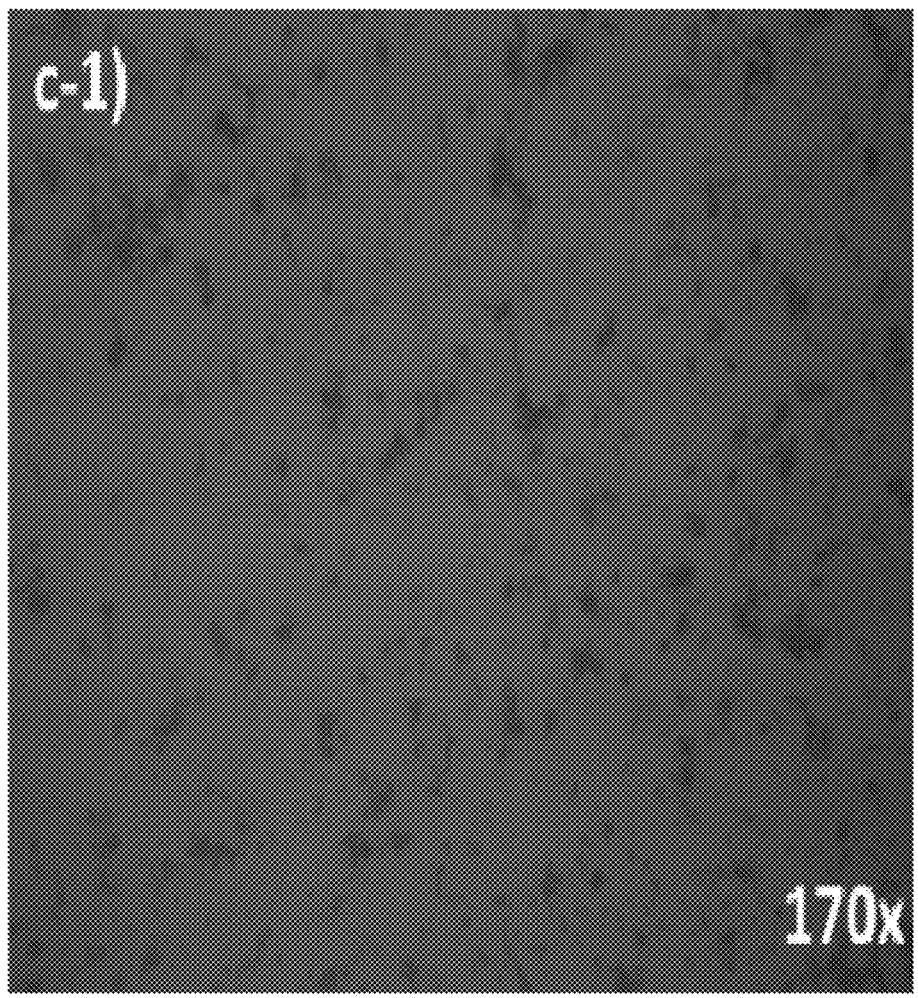
FIG. 2E shows an optical microscopy image of separated and fixed brain tumoral cells or astrocytoma cells stained by a papanicolaous-staining method with a magnification factor of 170×, according to an embodiment herein.
Figure 2F:
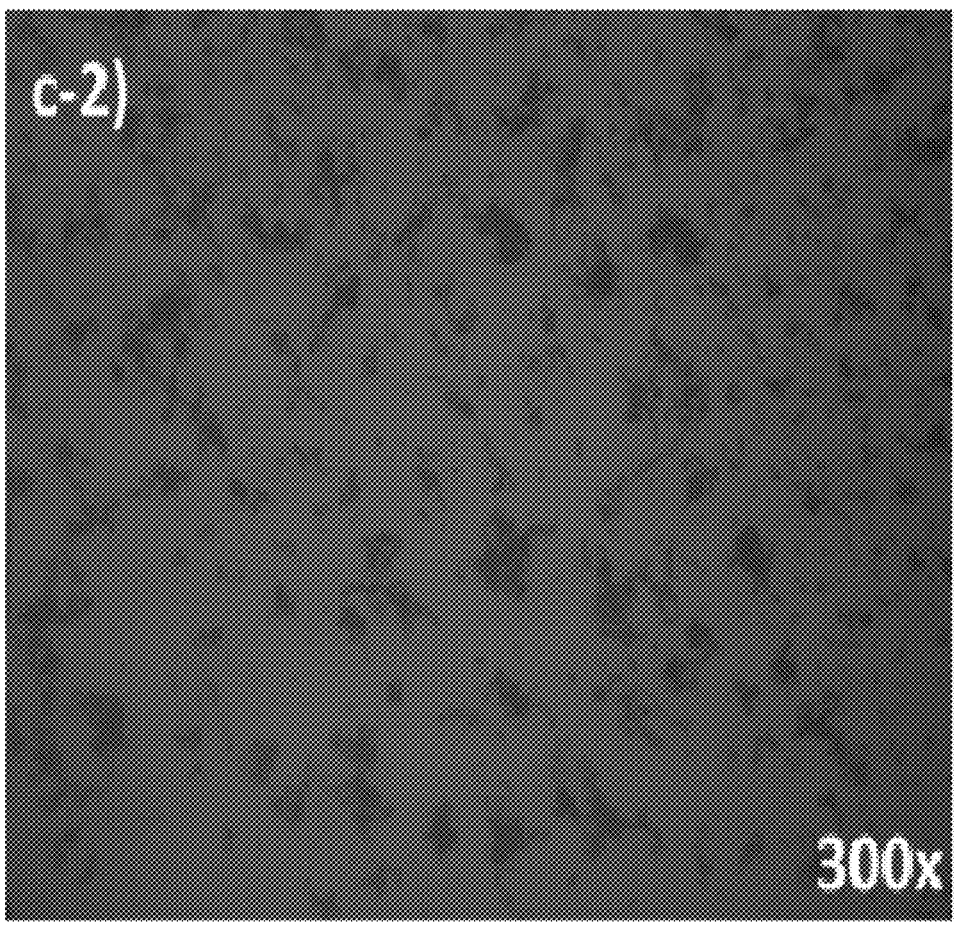
FIG. 2F shows an optical microscopy image of separated and fixed brain tumoral cells or astrocytoma cells stained by a papanicolaous-staining method with a magnification factor of 300×, according to an embodiment herein.

FIG. 2A and FIG. 2B show an optical microscopy images of the separated and fixed renal healthy cells with a magnification factor of 100× and 300× respectively, according to an embodiment herein, while FIG. 2C and FIG. 2D show an optical microscopy images of the renal caner or renal carcinoma cells stained by a papanicolaous-staining method. The images are shown with a magnification factor of 100× and 300× respectively, according to an embodiment herein. With respect to FIG. 2A-2D, it is observed that the renal cancer (renal carcinoma) cells as shown in FIG. 2C and FIG. 2D are more deformed and found to be larger than that of the renal healthy cells as shown in FIG. 2A and FIG. 2B FIG. 2E and FIG. 2F show an optical microscopy images of the separated and fixed brain tumoral cells or astrocytoma cells stained by a papanicolaous-staining method, according to an embodiment herein. With respect to FIG. 2E and FIG. 2F, the optical microscopy images of the separated and fixed brain tumoral cells or astrocytoma cells are shown with a magnification factor of 170× and 300× respectively. With respect to FIG. 2E and FIG. 2F, stained cancer cells are clearly visible. The cancer cells are observably larger and more deformed than healthy ones.

Figure 3:
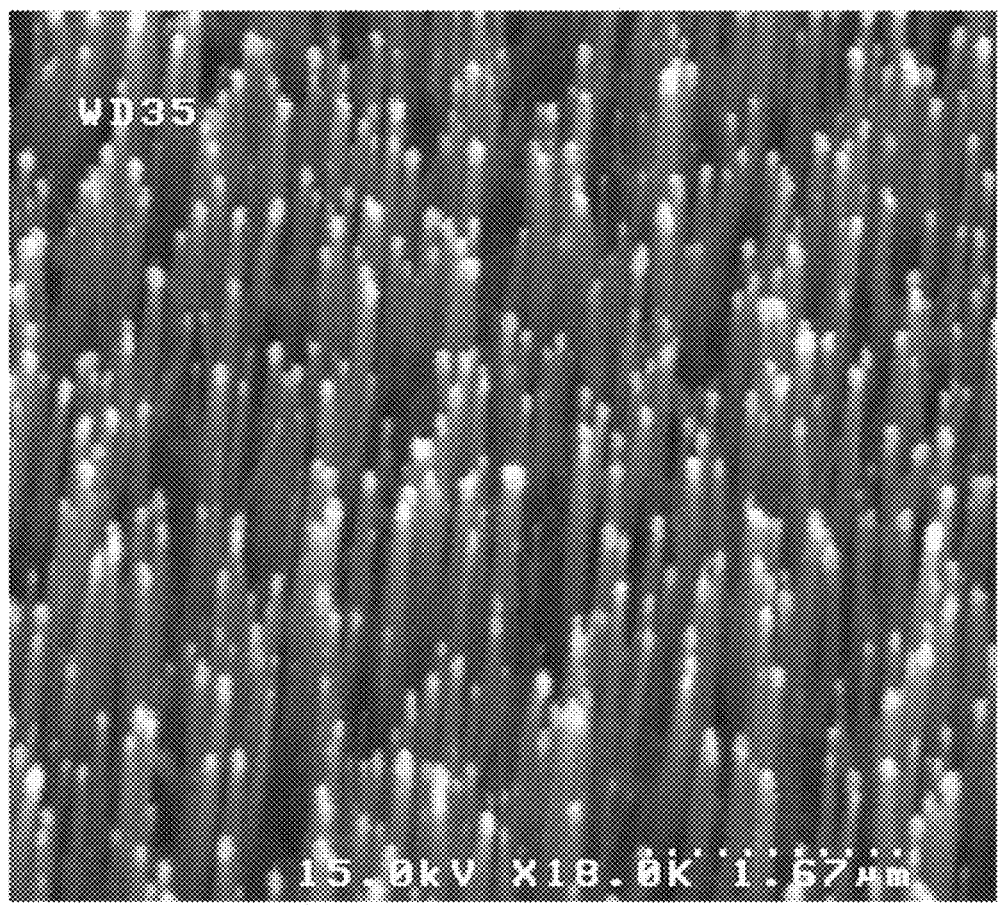
FIG. 3 shows a typical Scanning Electron Microscopic (SEM) image of vertically aligned Multiwall carbon nanotubes (MWCNTs) on silicon substrate, according to an embodiment herein.

FIG. 3 shows a typical Scanning Electron Microscopic (SEM) image of vertically aligned Multiwall carbon nanotubes (MWCNTs), according to an embodiment herein. In order to conduct the individual tests on the CNT-holding substrates, the separated solutions of benign and malignant cells were poured onto the target substrate surface by a peristaltic pump. The growth of MWCNT arrays was achieved using a direct-current plasma enhanced chemical vapor deposition technique. The H2 and C2H2 gases are mixed at a pressure of 1-5 torr and at a temperature of 550° C. A plasma power density of 5 W/cm2 is typically employed. A hydrogenation step is needed prior to the growth of CNTs to form the nano-sized islands of nickel acting as the catalyst layer for the growth of CNTs. The bright spots on the top side of such nanostructures are the nickel seeds. With respect FIG. 3, the bright spots on the top side of such nanostructures are the nickel seeds that act as catalyst for the growth of CNTs.

After pouring the cells onto the CNT arrays, they were dried in an air ambient. A Hitachi field emission scanning electron microscope was extensively used to study the prepared specimens.

Results and Discussions

Figure 4A:
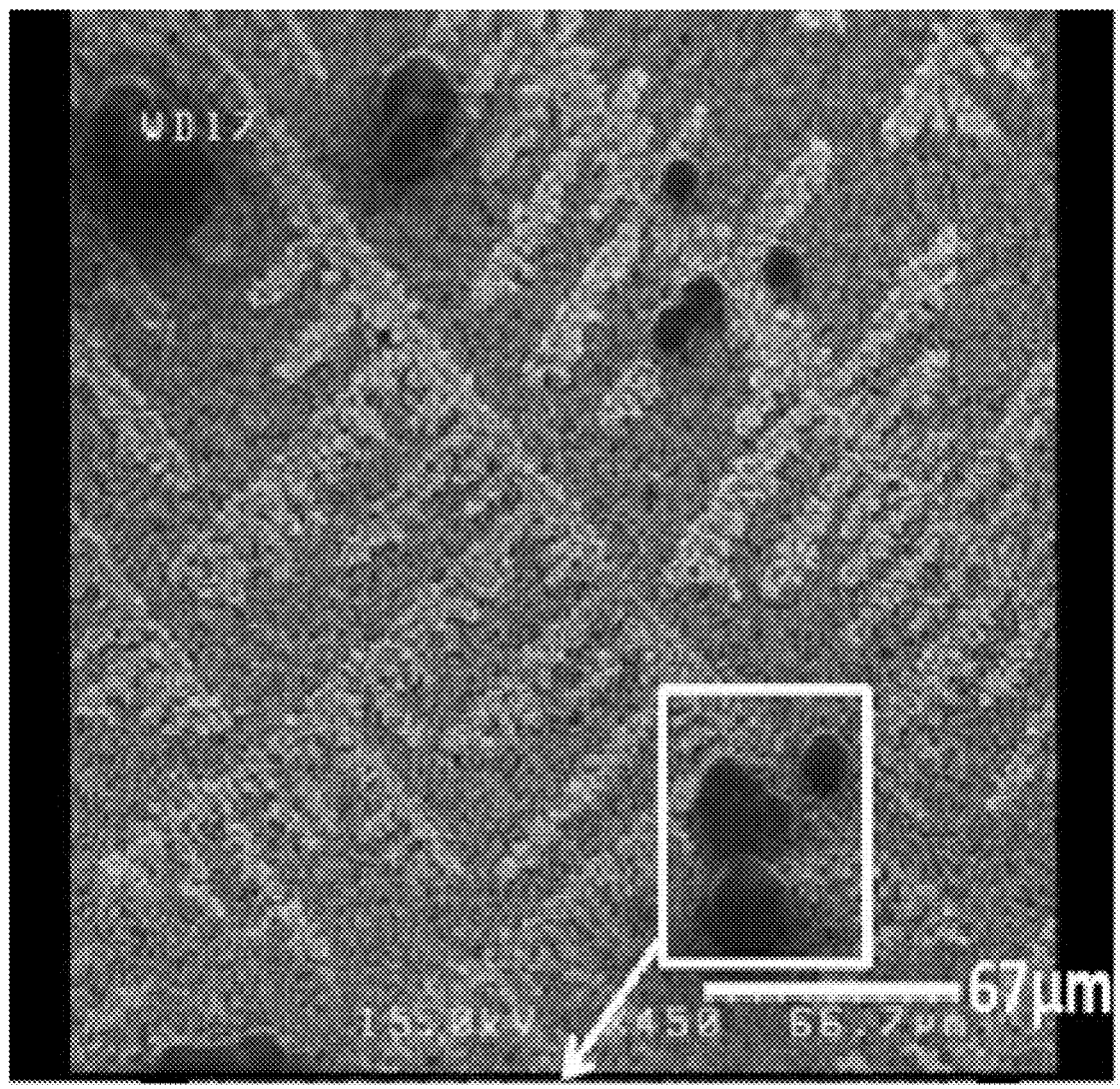
FIG. 4A shows a SEM image of the live colon cancer cell (HT29) entrapment on the carbon nanotubes arrays, according to an embodiment herein.
Figure 4B:
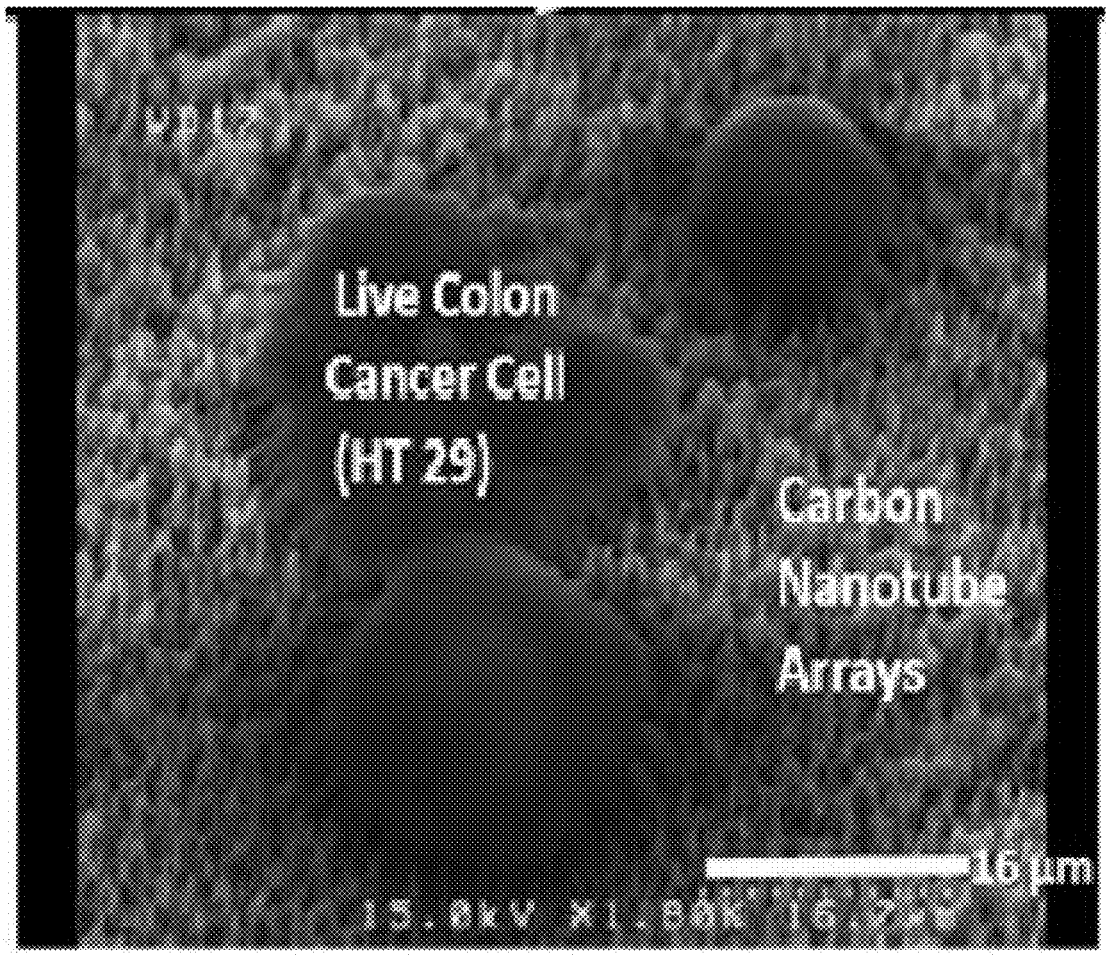
FIG. 4B shows a magnified view of the live colon cancer cell in a SEM image of the live colon cancer cell (HT29) entrapment on the carbon nanotubes array, according to an embodiment herein.

1) Entrapment of live cancer cells on aligned CNTs: FIG. 4A and FIG. 4B show SEM images of live HT29 cell entrapment on the carbon nanotubes array, according to an embodiment herein. FIG. 4A shows a SEM image of live HT29 cell entrapment on the carbon nanotubes array, according to an embodiment herein. With respect to FIG. 4A, some patterns are observed on the CNT holding substrate. The observed patterns on the CNT-holding substrate are believed to be due to the movement of the cancer cells prior to their complete entrapment and stoppage. FIG. 4B shows a SEM image of the HT29 cell entrapment on the carbon nanotubes array in a magnified scale, according to an embodiment herein. The entrapped live colon cancer cells i.e. HT 29 cell lines in a marked area in FIG. 4A is shown with an enlarged and magnified view in FIG. 4B. With respect to FIG. 4B, the entrapped live colon cancer cells i.e. HT 29 cell lines are observed after their complete entrapment and stoppage on the CNT array.

Figure 5A:
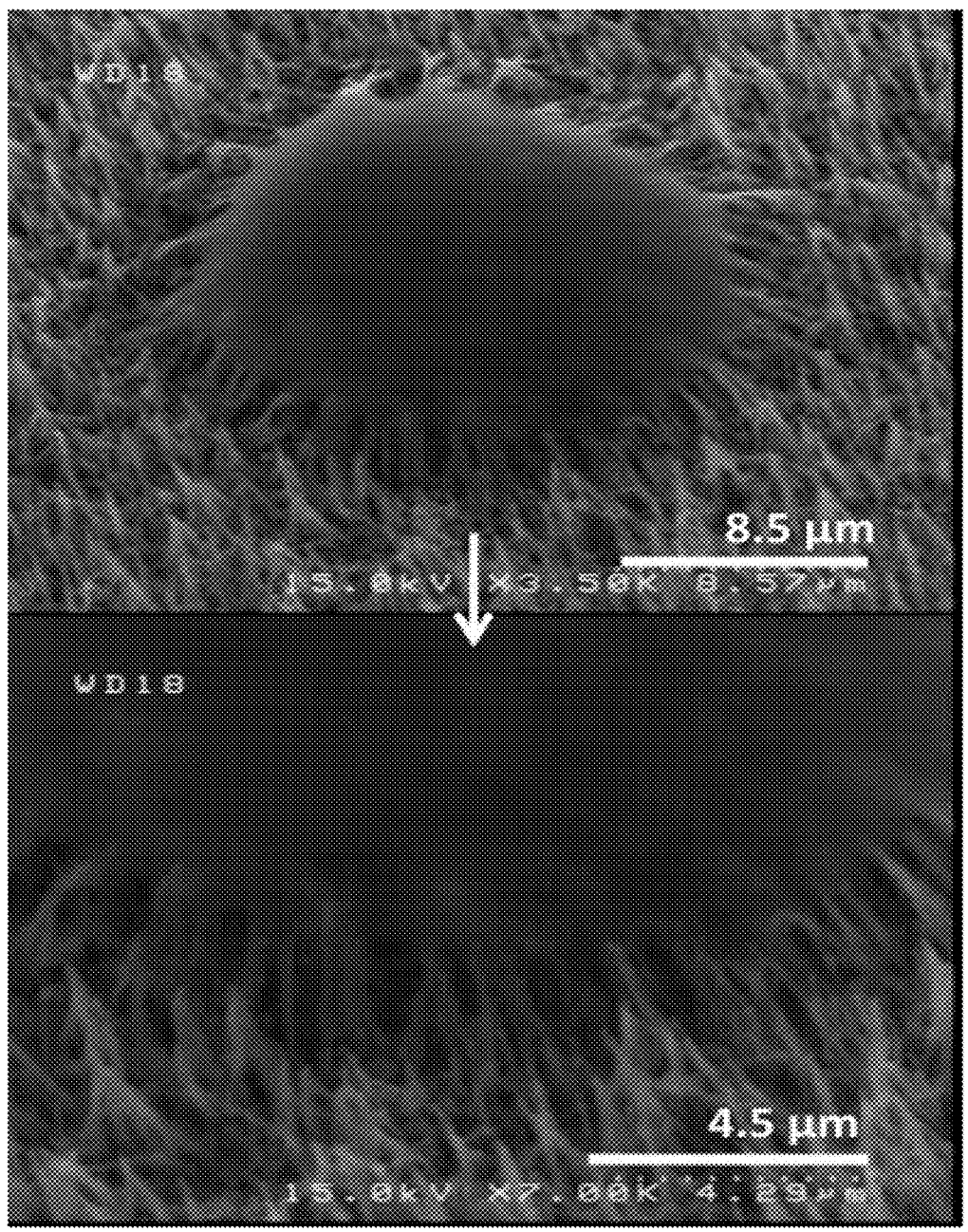
FIG. 5A shows a normal view and an enlarged view of live colon cancer cells in a SEM image of an entrapment of "live" colon cancer cells (HT 29) on MWCNT arrays, according to an embodiment herein.

FIG. 5A show a SEM image of an entrapment of "live" colon cancer cells (HT 29) on MWCNT arrays, according to an embodiment herein. With respect to FIG. 5A, the deflection of the vertically aligned carbon nanotubes after an entrapment of live colon cancer cells is shown. The CNT beams were deflected in large deflection mode. The tips of the carbon nanotubes are observable through the body of the cell.

Figure 5B:
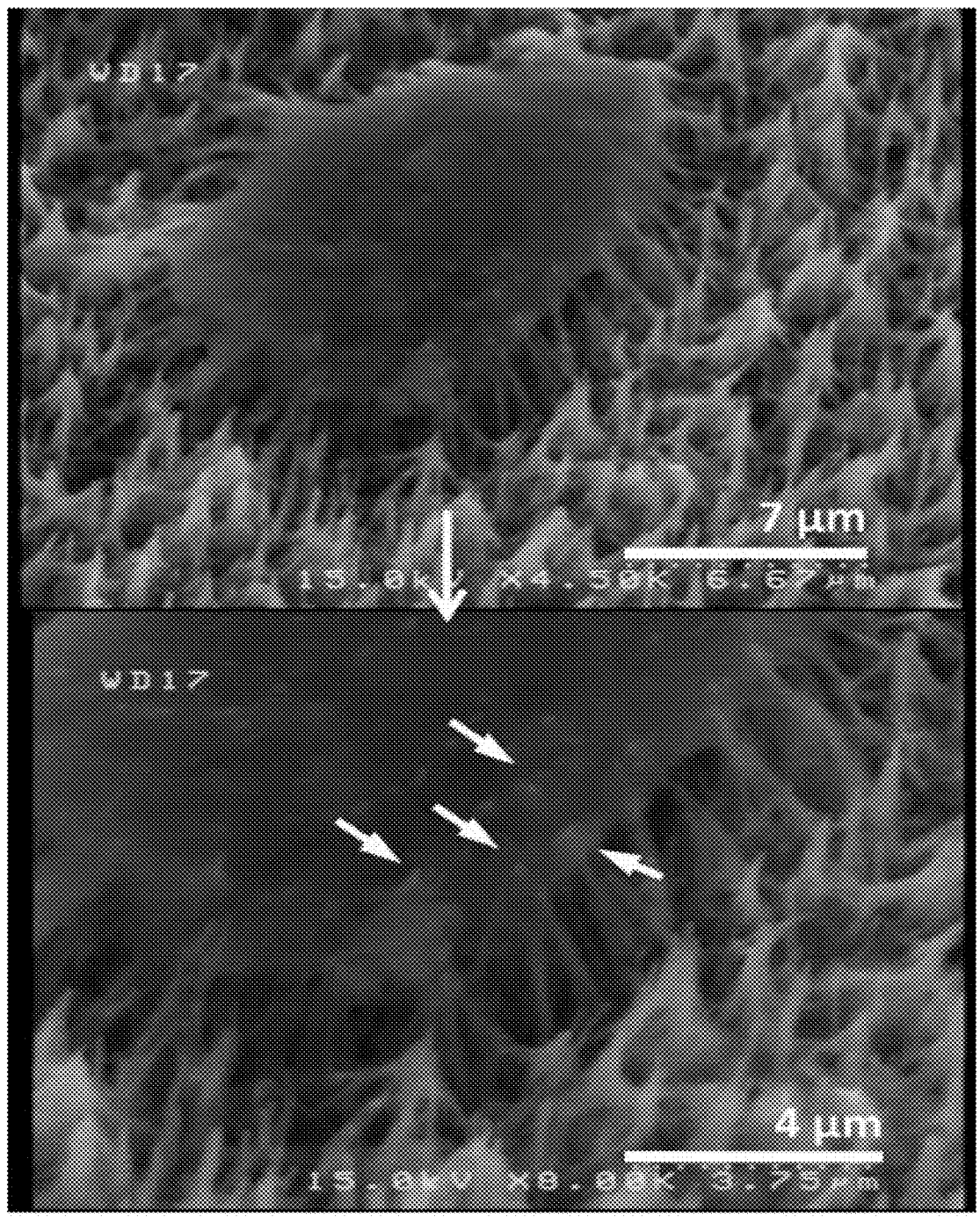
FIG. 5B shows a normal view and an enlarged view of live colon cancer cells in SEM image of an entrapment of "live" colon cancer cells (HT 29) on MWCNT arrays, according to an embodiment herein.

FIG. 5B show a SEM image of an entrapment of "live" colon cancer cells (HT 29) on MWCNT arrays, according to an embodiment herein. With respect to FIG. 5B, the CNT beams were deflected in a large deflection mode and their tips are observable through the body of the cells.

As shown from FIG. 5A and FIG. 5B, the malignant cells are entrapped onto the nanotube arrays and the deformability of these cells deflects CNTs in a large deflection mode. As mentioned, the physical differences between the cancerous cells and the healthy cells are mainly due to their cytoskeletal and the cell adhesion properties. As a result, the cancer cells are far less adhesive and more deformable than that of the normal cells. The observed results as shown in this figures FIG. 5A and FIG. 5B corroborate the fact that the entrapment of the cancerous cells onto the CNT-holding substrate is primarily due to the deformability of such cells and not due to their adhesive properties.

Effect of higher metastatic stages: In order to study the efficacy of the technique disclosed in the embodiments herein, the effect of two metastatic stages of the cancer cells present on the fraction of the entrapped cells on the CNT arrays were investigated. By conducting the entrapment experiments on live SW48 cell line (metastasis stage 4 of colon cancer cells) and comparing the results with HT29 cell line (stage 1 of metastasis of colon cancer cells), a significant increase by a factor of 2.5 in the level of entrapment of SW48 cells has been observed. The number of entrapped colon cancer cells of stage 1 was found to be 75 cells on an area of 273×273 µm$^2$ whereas the number of entrapped colon cancer cells of stage 4 was more than 170 on the same area and was higher for a higher stage of metastasis.

Figure 6A:
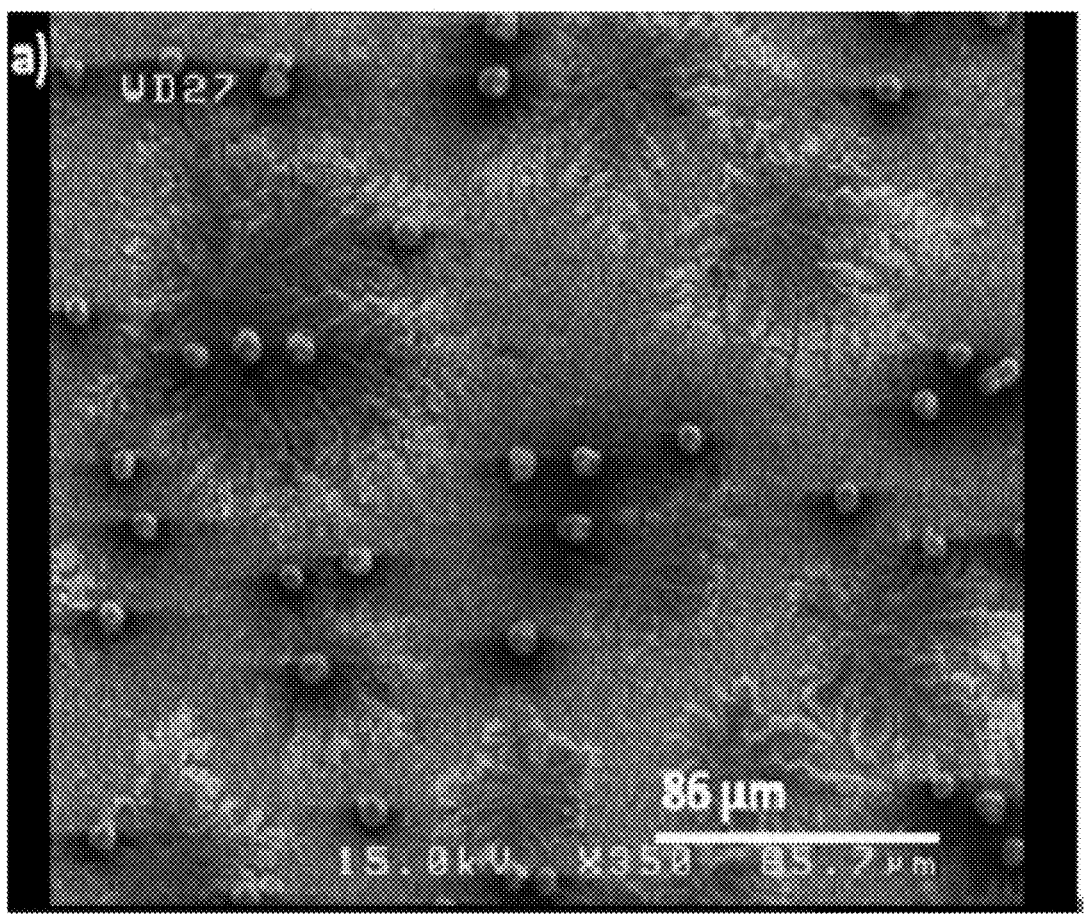
FIG. 6A shows a SEM image of trapped SW48 cell line (metastasis stage 4 of colon cancer cells) on a surface of CNT-coated substrates, according to an embodiment herein.
Figure 6B:
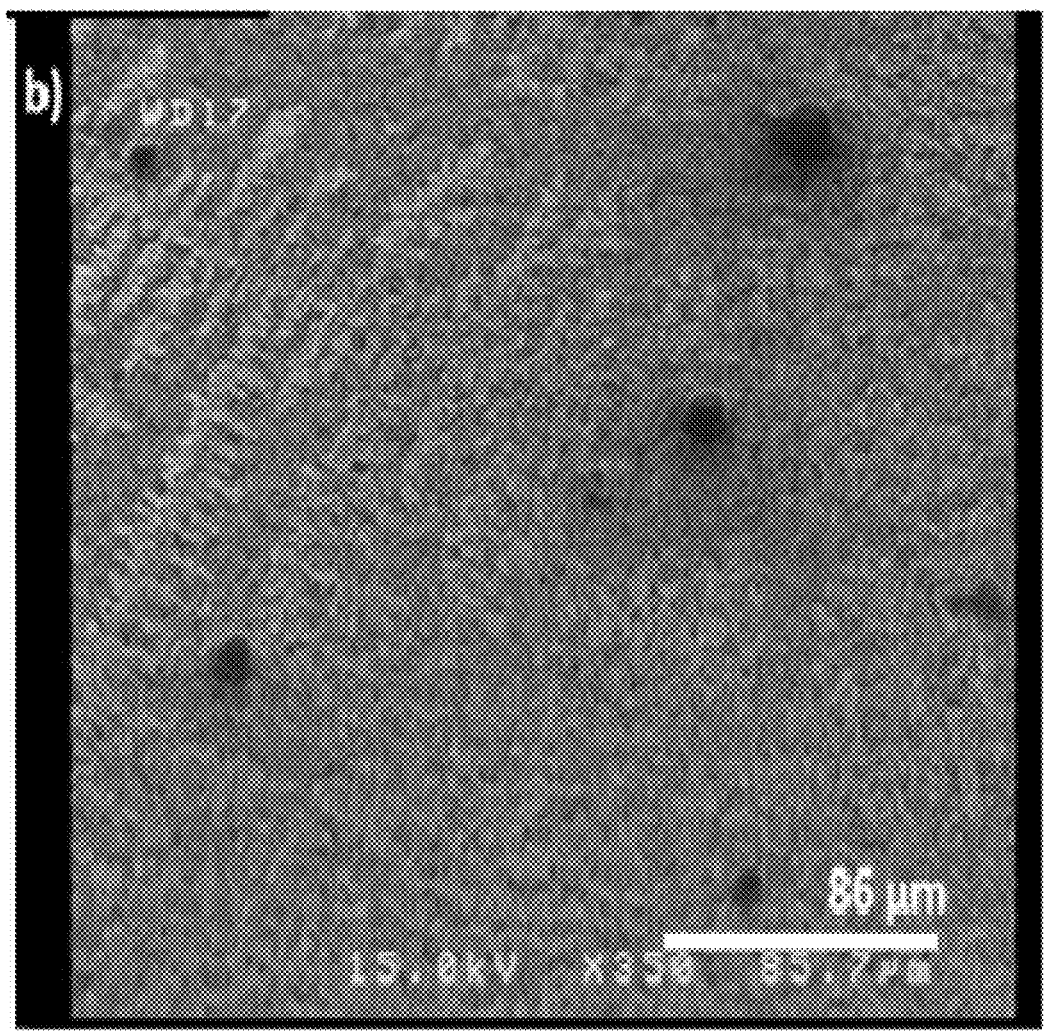
FIG. 6B shows a SEM image of trapped HT29 cell line (metastasis stage 1 of colon cancer cells) on a surface of CNT-coated substrates, according to an embodiment herein.

FIG. 6A shows a SEM image of entrapped SW48 cells on a surface of CNT-coated substrates and FIG. 6B shows a SEM image of entrapped HT29 cells on similar surfaces of CNT-coated substrates, according to an embodiment herein. With respect to FIG. 6A and FIG. 6B, a remarkable difference in the level of entrapment between the two stages of metastases is observed. The fraction of the entrapped highly metastatic cancer cells is obviously more than the one corresponding to a lower metastatic stage. The cancer cells with the higher metastatic stages have more deformable structures and are much softer than that of the lower metastatic ones. This fact was proved/displayed/indicated in the SEM image of the entrapped SW48 cells in comparison with HT29 cells as shown in FIG. 6B. For a better understanding of this phenomenon, the FIG. 6A and FIG. 6B display the several SEM images of SW48 cells on the CNT arrays with a large surface of 0.45×0.45 cm$^2$ where a large and highly populated number of entrapped cells are detected.

Figure 7A:
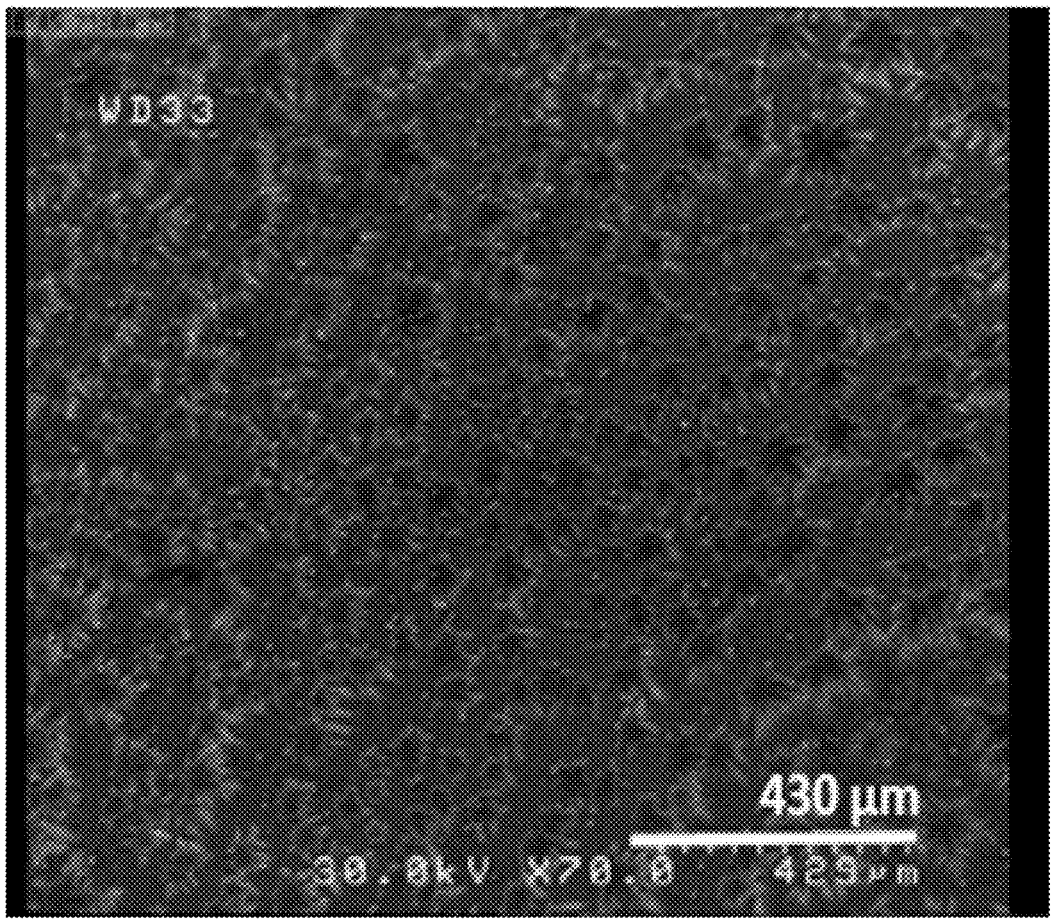
FIG. 7A shows a SEM image of the entrapped SW48 (metastasis stage 4 of colon cancer cells) cancer cells on CNT arrays in a large scale of 430 μm, according to an embodiment herein.
Figure 7B:
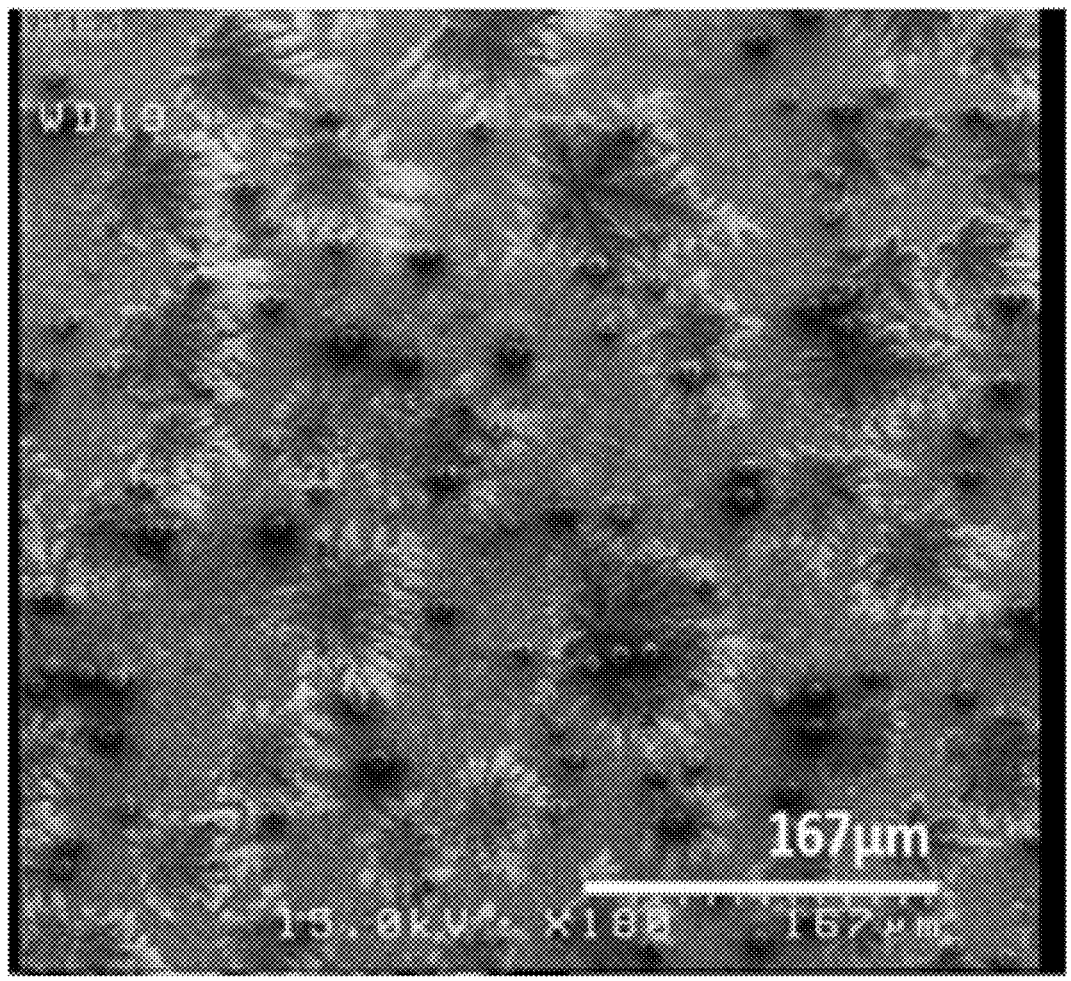
FIG. 7B shows a SEM image of the entrapped SW48 (metastasis stage 4 of colon cancer cells) cancer cells on CNT arrays on an enlarged scale of 167 μm, according to an embodiment herein.
Figure 7C:
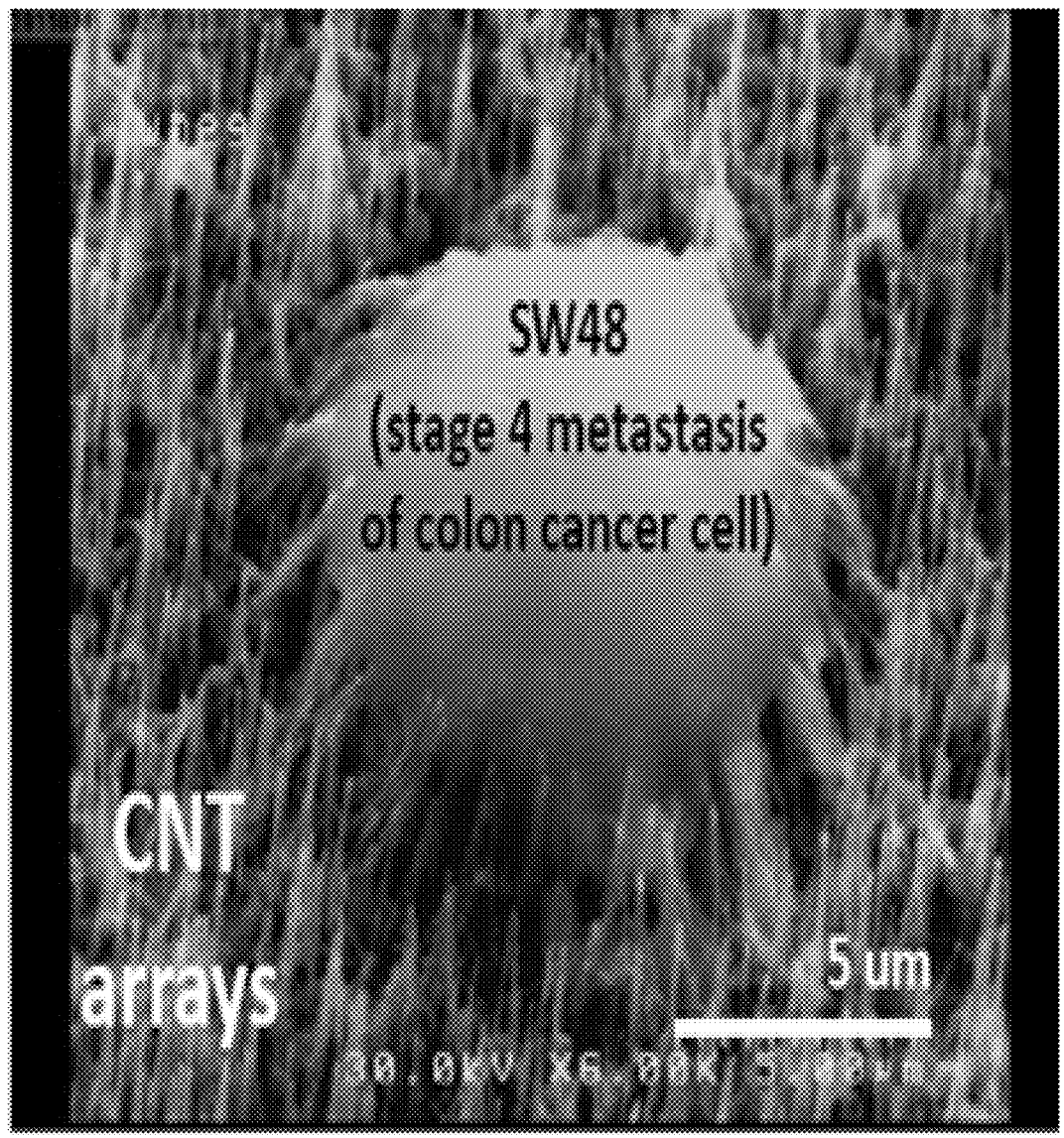
FIG. 7C shows a magnified view of a SEM image of the entrapped SW48 (metastasis stage 4 of colon cancer cells) cancer cells on CNT arrays on a further enlarged scale of 5 μm, according to an embodiment herein.

FIG. 7A-FIG. 7C show the SEM images of the entrapped SW48 cells on the CNT arrays in large scales, according to an embodiment herein. FIG. 7A shows a SEM image of the entrapped SW48 cells on the CNT arrays on a scale of 430 µm, according to an embodiment herein. With respect to FIG. 7A, the entrapped SW48 cells on the CNT arrays are visible. The SW48 cell line of colon cancer cell is at a stage 4 of metastasis.

FIG. 7B shows a magnified SEM image of the entrapped SW48 cells on the CNT arrays on a scale of 167 µm, according to an embodiment herein. With respect to FIG. 7B, the entrapped SW48 cells on the CNT arrays are more clearly visible. The patterns formed due to the movement of the cells are visible.

FIG. 7C shows a further enlarged and magnified SEM image of the entrapped SW48 cells on the CNT arrays on a scale of 5 µm, according to an embodiment herein. With respect to FIG. 7C, the entrapment of the SW48 cell line of colon cancer cell at stage 4 of metastasis is shown more clearly in an enlarged and magnified view.

Effect of surface heating: The MWCNT-holding substrates were exposed to a thermal irradiation prior to a pouring of the cell solution and the amount of the entrapment of the cancer cells on the substrate after an irradiation with an Infra Red (IR) lamp was measured. It is observed that there is a remarkable increase in the fraction of entrapped HT 29 cancer cells on nanotube arrays heated with IR lamp.

Figure 8A:
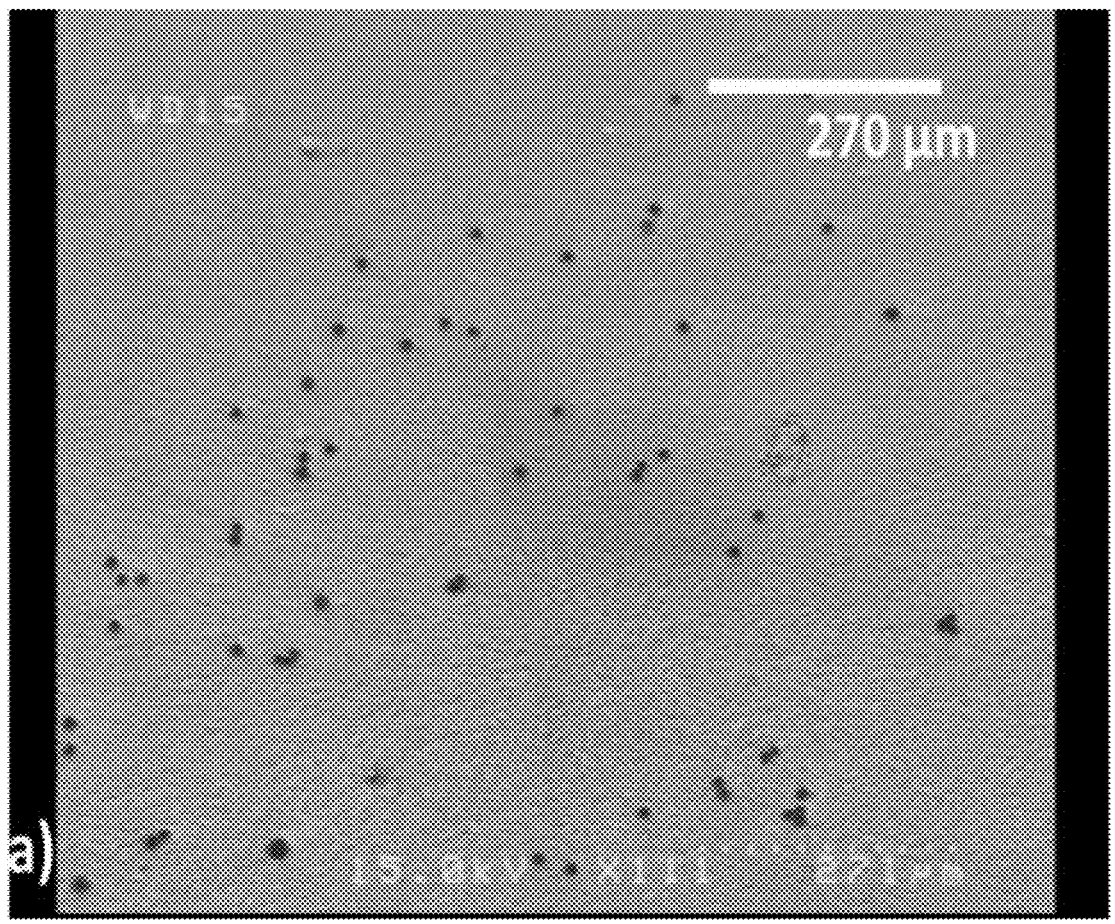
FIG. 8A shows a SEM image of the entrapped HT29 live colon cancer cells on the CNT arrays at a substrate surface which is not irradiated with by Infra Red (IR) lamp according to an embodiment herein.
Figure 8B:
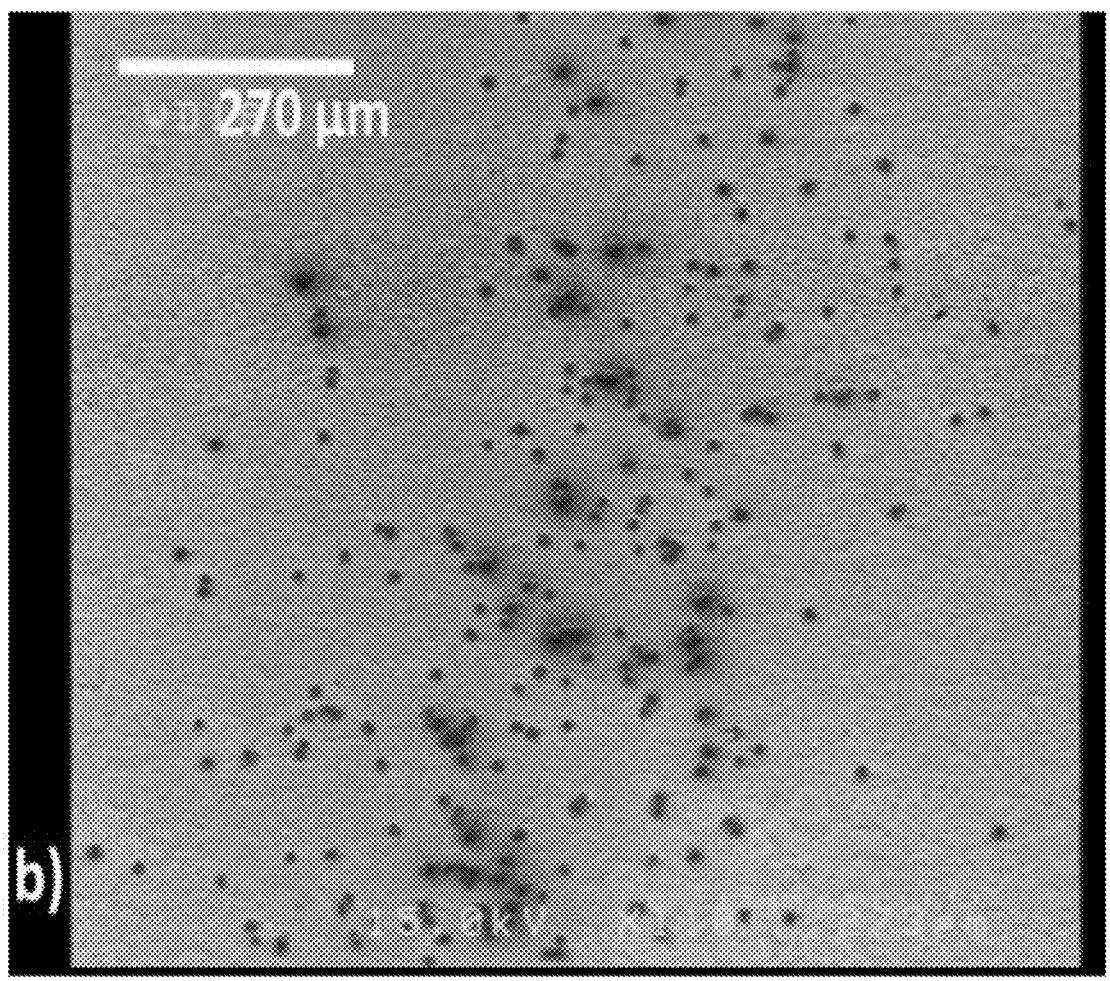
FIG. 8B shows a SEM image of the entrapped HT29 live colon cancer cells on the CNT arrays at a substrate surface which is irradiated with by Infra Red (IR) lamp for 3.5 minutes, according to an embodiment herein.

FIG. 8A and FIG. 8B shows an effect of thermal irradiation on the entrapment of HT29 live colon cancer cells on the CNT arrays when the substrate surface is heated before the cell solution is poured, according to an embodiment herein. FIG. 8A shows a SEM image of the MWCNT arrays showing the entrapment of "live" HT 29 cancer cells on a non-irradiated surface. FIG. 8B shows a SEM image of the MWCNT arrays showing the entrapment of "live" HT 29 cancer cells on a surface when the surface is irradiated with IR lamp for 3.5 minutes, before the pouring of a cell solution, according to an embodiment herein. With respect to FIG. 8A and FIG. 8B, it is found that the fraction of entrapped cancer cells on the irradiated surface is more than that on a non irradiated surface. The fraction of the entrapped cancer cells is increased from 30% to about 90% by heating the surface of the substrate for 3-5 min by an IR lamp. The amount of entrapped cells after IR irradiation is increased by about a factor of three. In both the cases, the flow rate of the solution poured on the substrate was about 5 cc/min.

Effect of cancer cell fixation: In another experiment, the HT 29 colon cancer cells were fixed by a 10% glutaraldehyde solution.

Figure 9A:
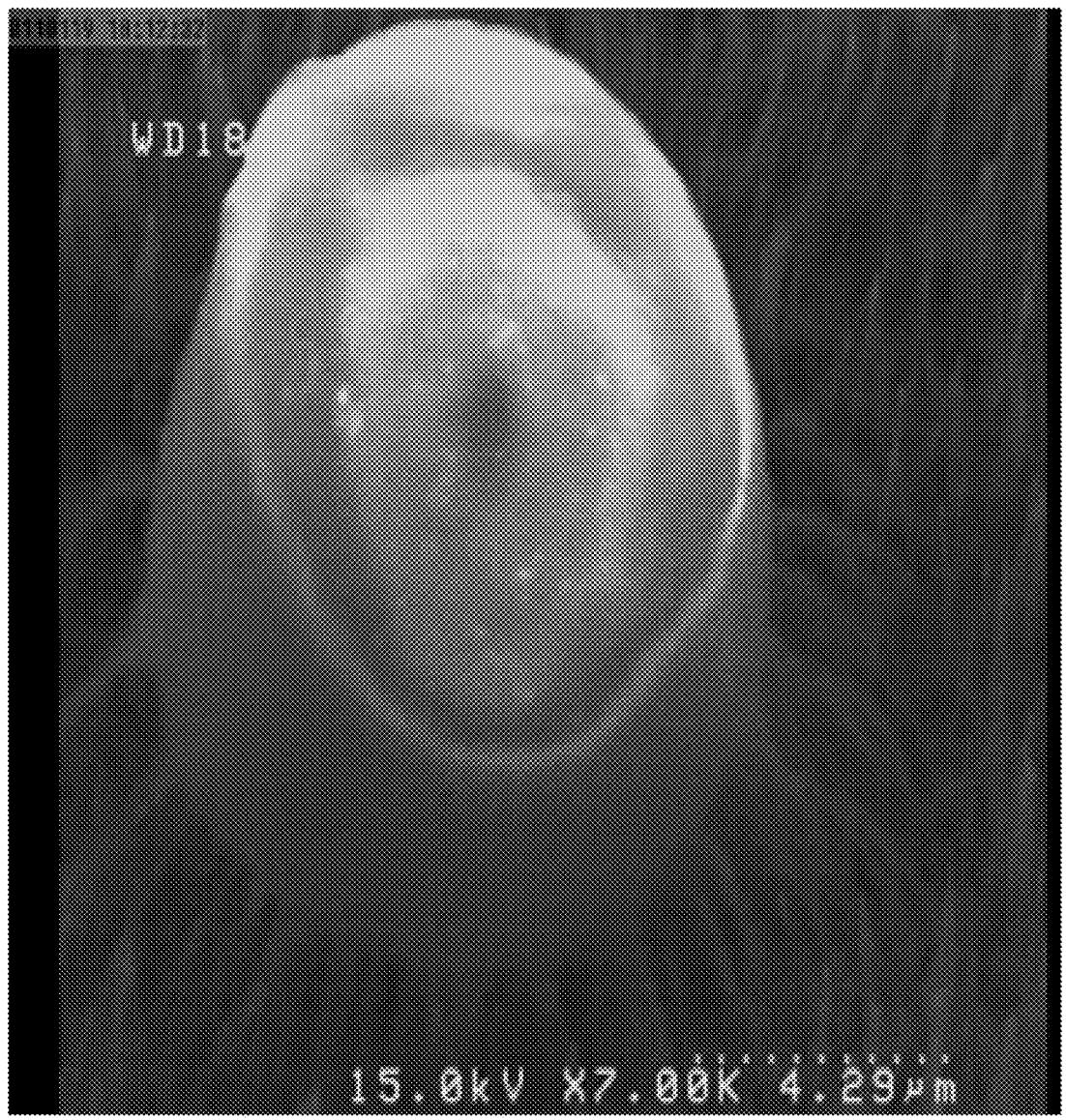
FIG. 9A shows an SEM image of several entrapped fixed colon cancer cells at one region (first region) of CNT arrays with a scale of 4.29 μm, according to an embodiment herein.
Figure 9B:
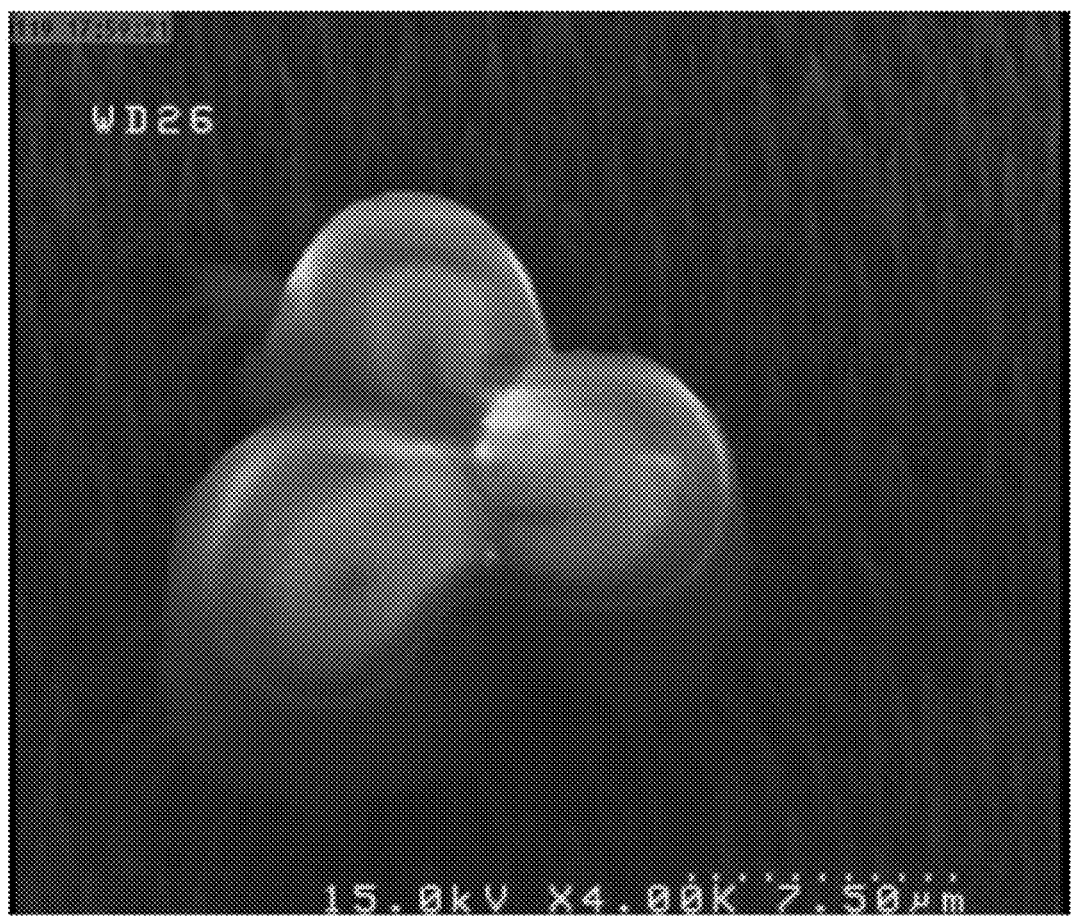
FIG. 9B shows an SEM image of several entrapped fixed colon cancer cells at one region (second region) of CNT arrays with a scale of 7.50 μm, according to an embodiment herein.
Figure 9C:
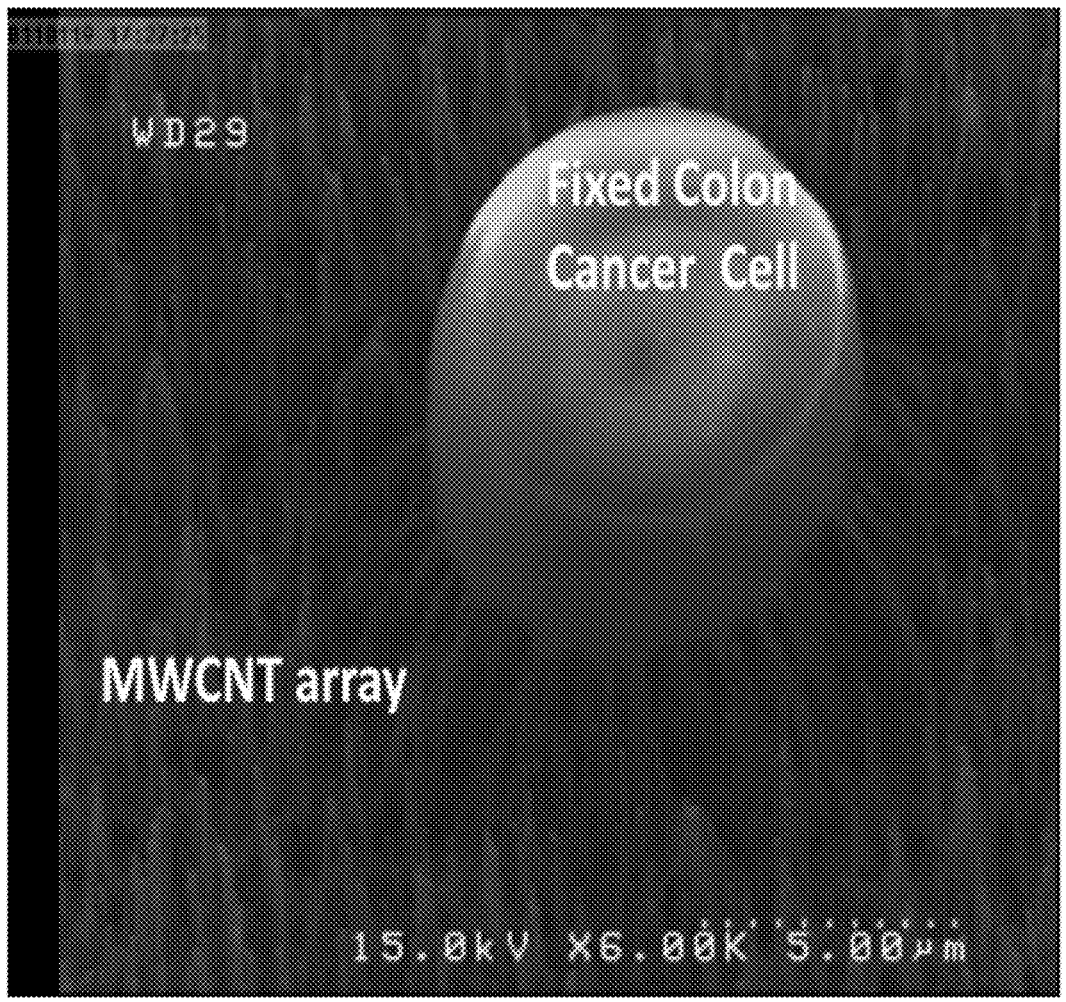
FIG. 9C shows an SEM image of several entrapped fixed colon cancer cells at one region (third region) of CNT arrays with a scale of 5.00 μm, according to an embodiment herein.
Figure 9D:
FIG. 9D show SEM image of several entrapped fixed colon cancer cells at one region (fourth region) of CNT arrays with a scale of 2.31 μm, according to an embodiment herein.

FIG. 9A shows a SEM image of several entrapped fixed colon cancer cells on one region of the CNT arrays at a scale of 4.29 µm, according to an embodiment herein. FIG. 9B shows a SEM image of several entrapped fixed colon cancer cells on another region of the CNT arrays at a scale of 7.50 µm, according to an embodiment herein. FIG. 9C shows a SEM image of several entrapped fixed colon cancer cells on another region of the CNT arrays at a scale of 5 µm, according to an embodiment herein. FIG. 9D shows a SEM image of several entrapped fixed colon cancer cells on another region of CNT arrays at a scale of 2.31 µm, according to an embodiment herein.

With respect to FIG. 9A-FIG. 9D, the effect of glutaraldehyde fixation in the quality of the SEM images is discernible where the nucleus of the cell is easily distinguishable.

The HT29 cells fixed in the glutaraldehyde solution were exposed to the CNT arrays where a remarkably lower entrapment of such species (colon cancer cells) in comparison with that of the live or healthy cells was observed. This observation corroborates the previous findings that the force required to compress the fixed cells is at least 20-50 times higher than that for living or dead cells. It shows that the fixed cells are almost 20-50 times more rigid than the living cells. As a result the entrapment fraction of the fixed cells is expected to be less than that of the live ones.

Figure 10A:
FIG. 10A shows a SEM image of entrapped fixed HT29 colon cancer cells on CNT arrays at a scale of 273 μm, according to an embodiment herein.
Figure 10B:
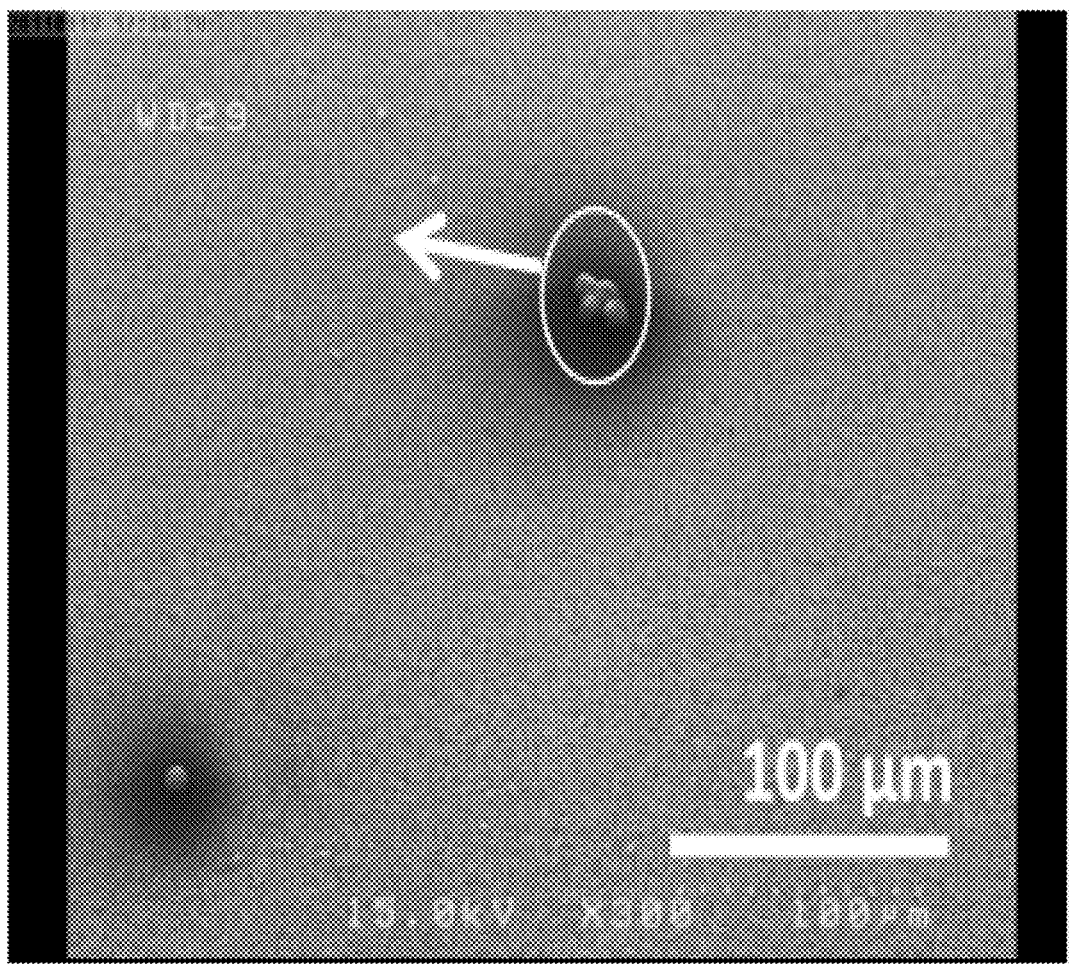
FIG. 10B shows a SEM image of entrapped fixed HT29 colon cancer cells on CNT arrays at a scale of 100 μm, according to an embodiment herein.
Figure 10C:
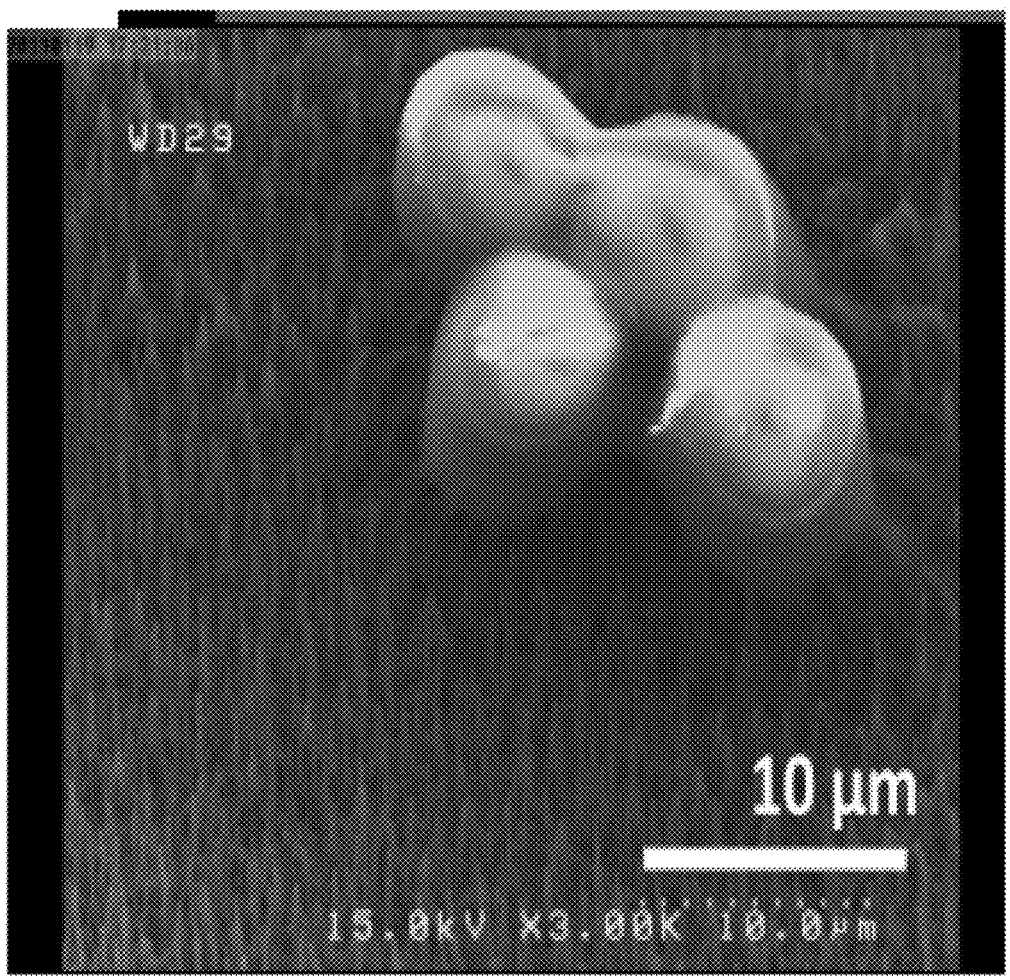
FIG. 10C shows a SEM image of entrapped fixed HT29 colon cancer cells on CNT arrays at a scale of 10 μm, according to an embodiment herein.

FIG. 10A-FIG. 10C show the SEM micrographs of fixed HT29 cells (colon cancer cells) on the CNT arrays, according to an embodiment herein. FIG. 10A shows a SEM image of fixed HT29 cells at a scale of 273 µm, according to an embodiment herein. FIG. 10B shows a SEM image of fixed HT29 cells at a scale of 100 µm, according to an embodiment herein. FIG. 10C shows a SEM image of fixed HT29 cells at a scale of 10 µm, according to an embodiment herein. With respect to FIG. 10A-FIG. 10C, the amount of the entrapped cells as shown in FIG. 10 A is clearly lower than the amount or level or value the entrapment of live HT29 colon cancer cells shown in FIG. 8A, for the cell solution of same concentration and same flow rate. So the fixation of the cancer cells resulted in increment of cell rigidity and decrement of cell entrapment on CNT arrays.

On the other hand, it is deduced from the above observation that the transformation of the cancer cells to higher metastatic stages will result in an increase in the cell deformability, softness and finally a rise of cell entrapment on the CNT arrays is observed.

Figure 11:
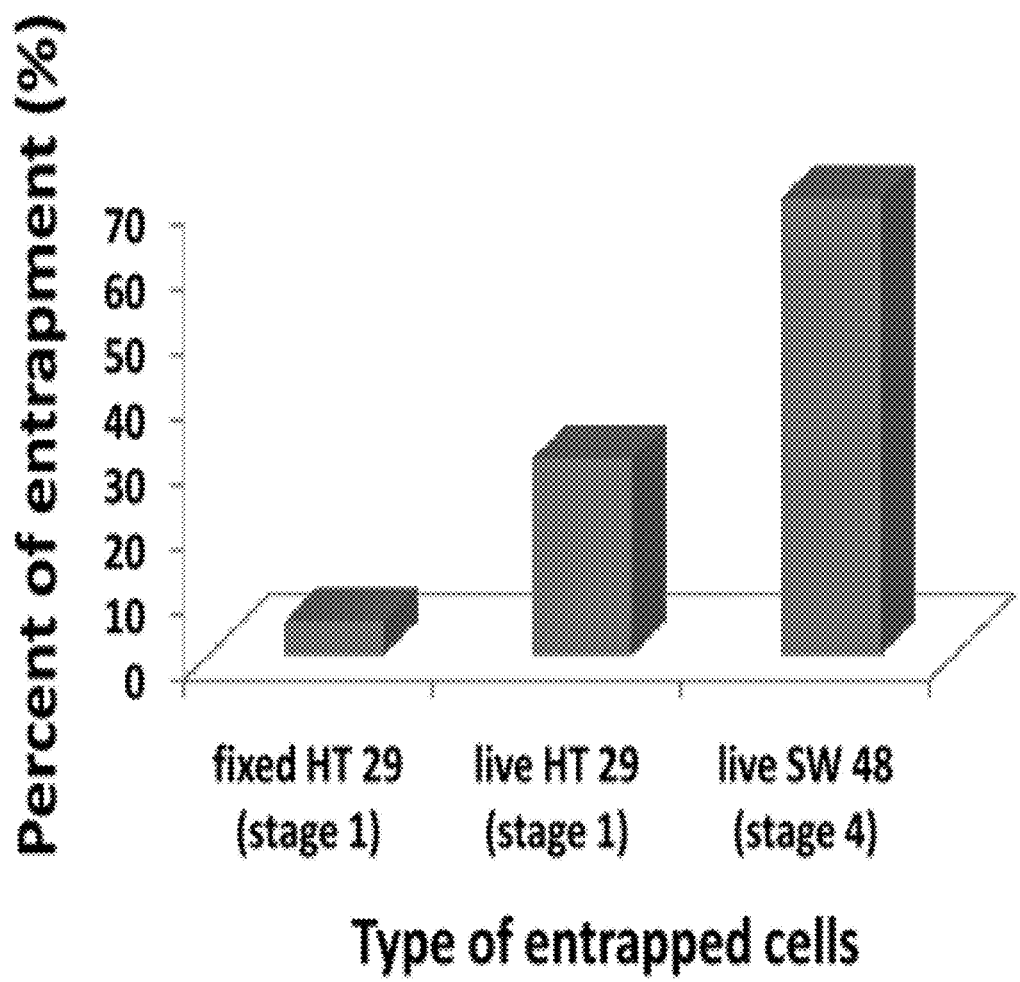
FIG. 11 shows a graphical representation illustrating a comparison of the fractions of entrapped cells of different types at various stages of metastases, according to an embodiment herein.

FIG. 11 shows a graphical representation illustrating a comparison of the fractions of entrapped cells with respect to the various stages of metastases of cancer cells, according to an embodiment herein. With respect to FIG. 11, a comparison of the entrapment percentages of the different stages of the metastatic transformations and fixation of the cancer cells is provided in a histogram style. A higher metastatic transformation (SW48 vs. HT29) results in an observable increase in the fraction of cell entrapment of live SW 48 cells (stage 4 of metastatis) from about 30% to more than 70%. For the fixed HT 29 cells (stage 1 of metastatis) and live HT 29 cells (stage 1 of metastatis), there is a decrease in cell entrapment percentage levels. The cell entrapment percentage is decreased from 30% for live HT29 to 5% for fixed HT29. The concentration and pouring flow rate of the cell solution were the same for all the three samples.

Figure 12:
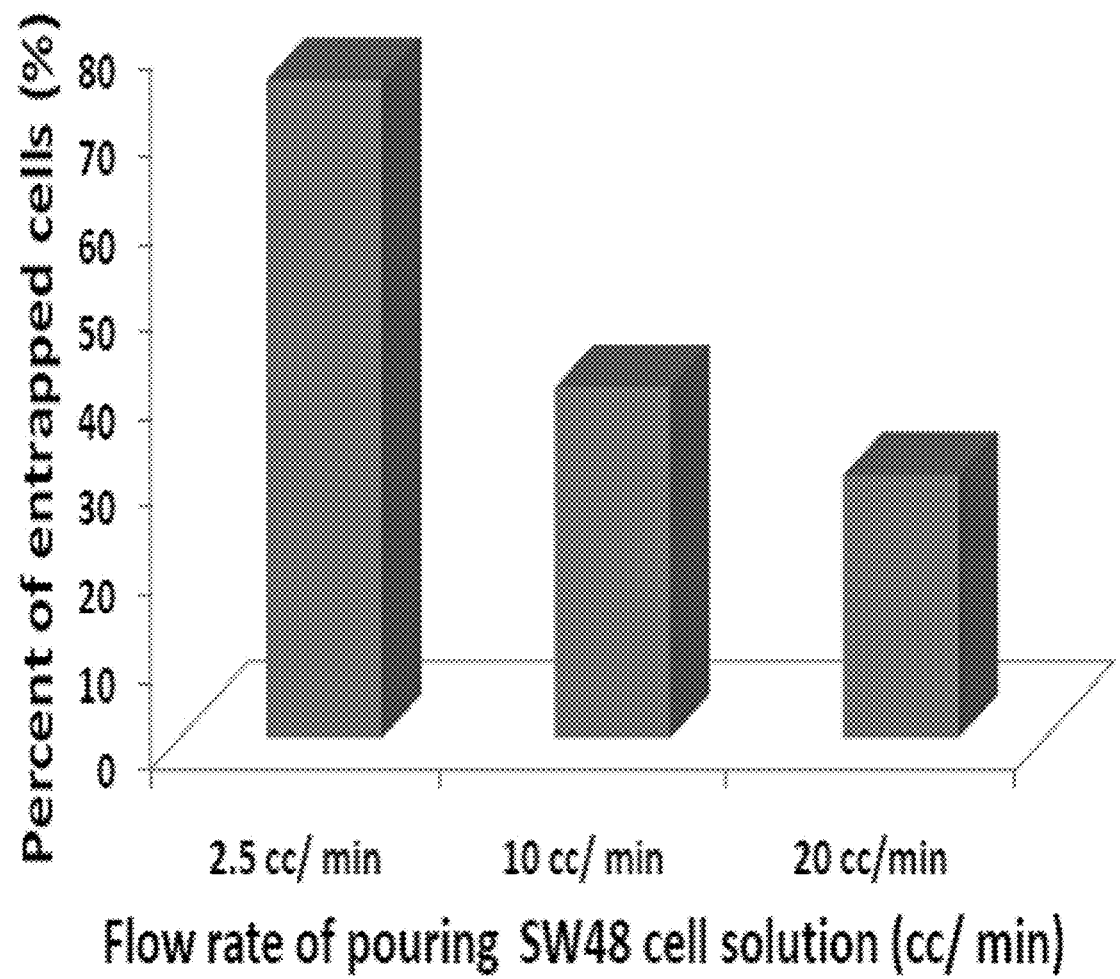
FIG. 12 shows a graphical representation illustrating the percentages of entrapped cells with respect to different flow rates of cell solutions, according to an embodiment herein.

Effect of solution flow rate: The rise in the flow rate of the cell solution poured on the substrate results in a reduction in the entrapment of the cells. A cell solution with a same cell concentration of live SW48 cell line is poured on the substrate at three different flow rates of 2.5 cc/min, 10 cc/min and 20 cc/min by a peristaltic pump. FIG. 12 shows a graphical representation illustrating a relationship between the percentages of the entrapped cells and the flow rates of the cell solutions poured on a substrate. With respect to FIG. 12, the fractions of entrapped cells were 75%, 40% and 30% for the flow rates of 2.5 cc/min, 10 cc/min and 20 cc/min respectively. The increment in a flow rate of the cell solution results in an increase of the cell speed during an interaction with the CNT arrays so that a lesser amount of the cells only have a sufficient time to get entrapped on the nanotube beams. As shown in FIG. 12, an increase in the flow rate of the pumped solution pump from 2.5 cc/min to 20 cc/min, results in a drop in the fraction of cell entrapment from 75% to 30%.

Entrapment of fixed renal cancer (RC) vs. renal healthy cells: For a clinical test, both the renal cancer cells and the renal healthy cells were removed from a known renal carcinoma case and prepared by the process which was mentioned in the previous sections. By repeating the experiments with both the healthy renal cells and the renal cancerous cells, one can observe the selective entrapment of the renal cancerous cells on the nanotube arrays.

Figure 13A:
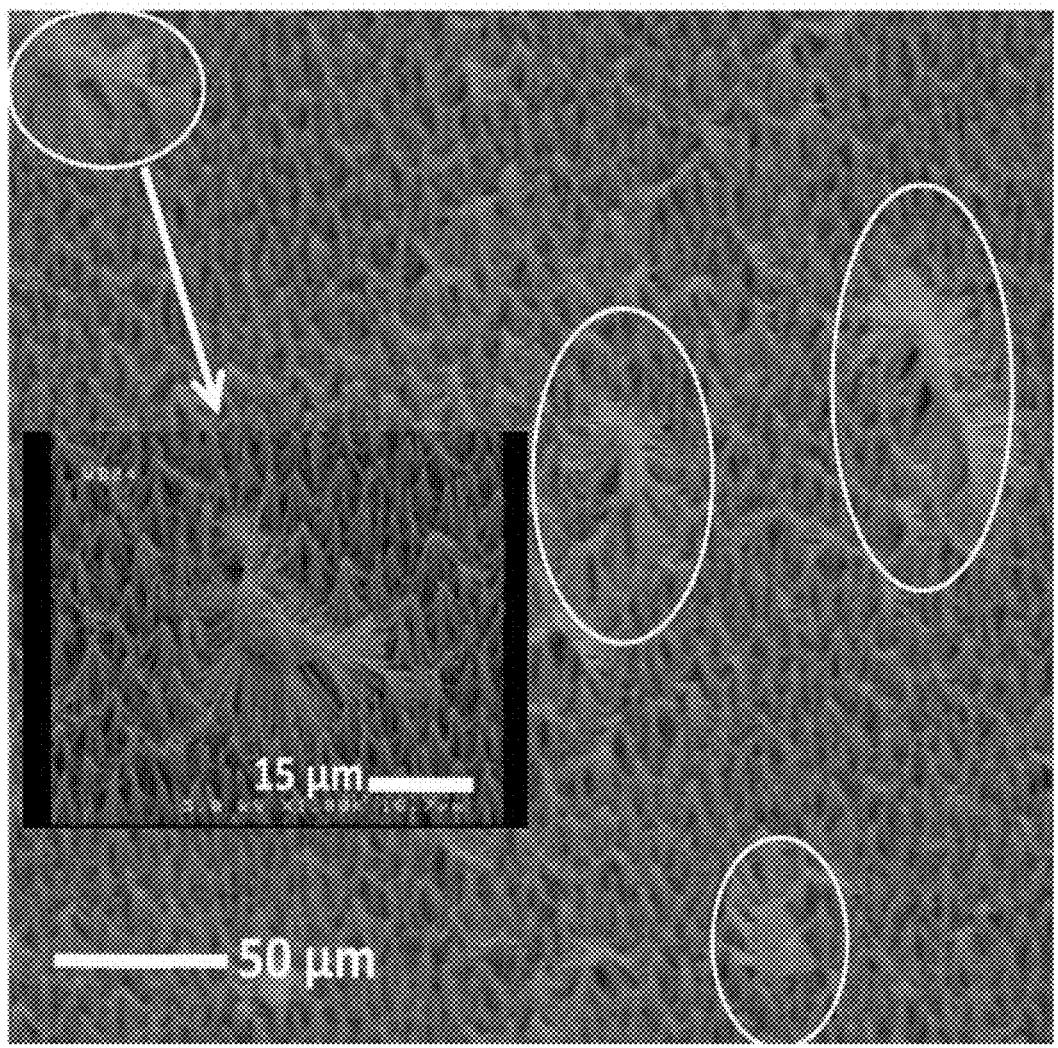
FIG. 13A shows a normal view and an enlarged view of a SEM image of the entrapment of renal cancer cells, according to an embodiment herein.
Figure 13B:
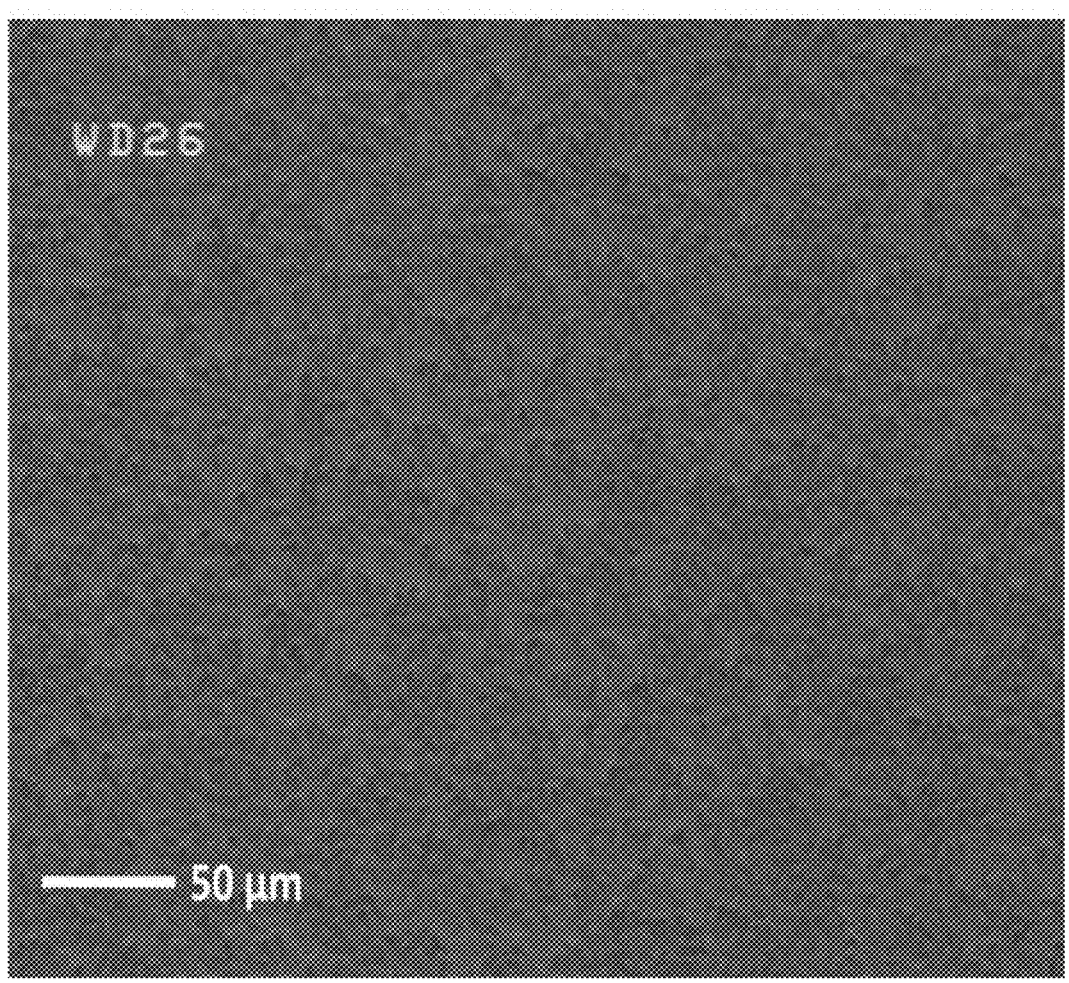
FIG. 13B shows a SEM image of the entrapment of the benign renal cells, according to an embodiment herein.

FIG. 13A and FIG. 13B show the SEM images of the entrapment of the renal cancer cells and the renal benign cells, according to an embodiment herein. FIG. 13A shows a SEM image of the entrapment of the renal cancer cells, according to an embodiment herein. FIG. 13B shows a SEM image of the entrapment of the renal benign cells, according to an embodiment herein. With respect to FIG. 13A and FIG. 13B, no entrapment of the renal benign cells was observed evidencing a selective entrapment of the renal cancerous cells as opposed to the healthy cells.

Figure 14A:
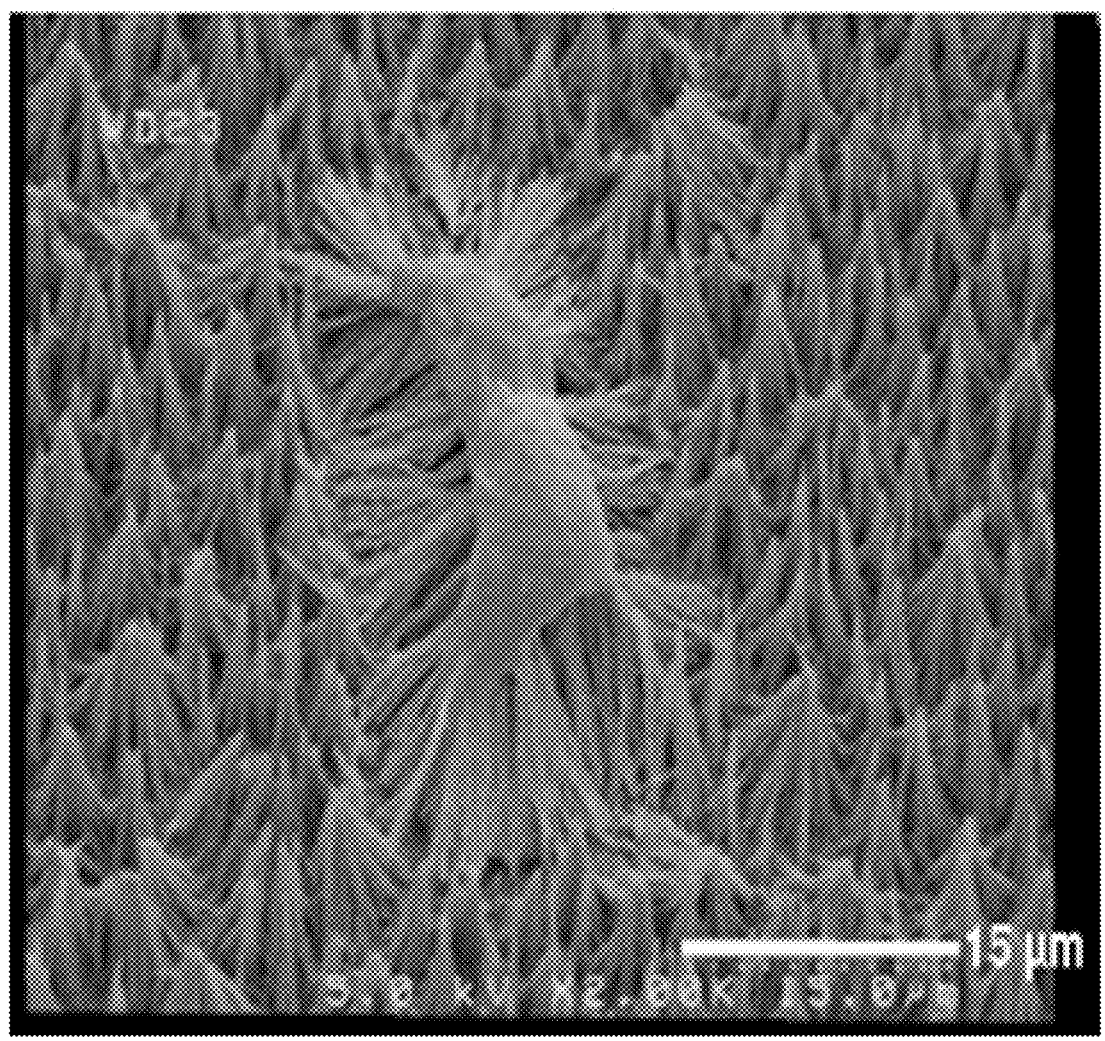
FIG. 14A shows a SEM image of the entrapment of several renal carcinoma cells on MWCNT arrays with large deflection angles of CNT beams from one side, according to an embodiment herein.
Figure 14B:
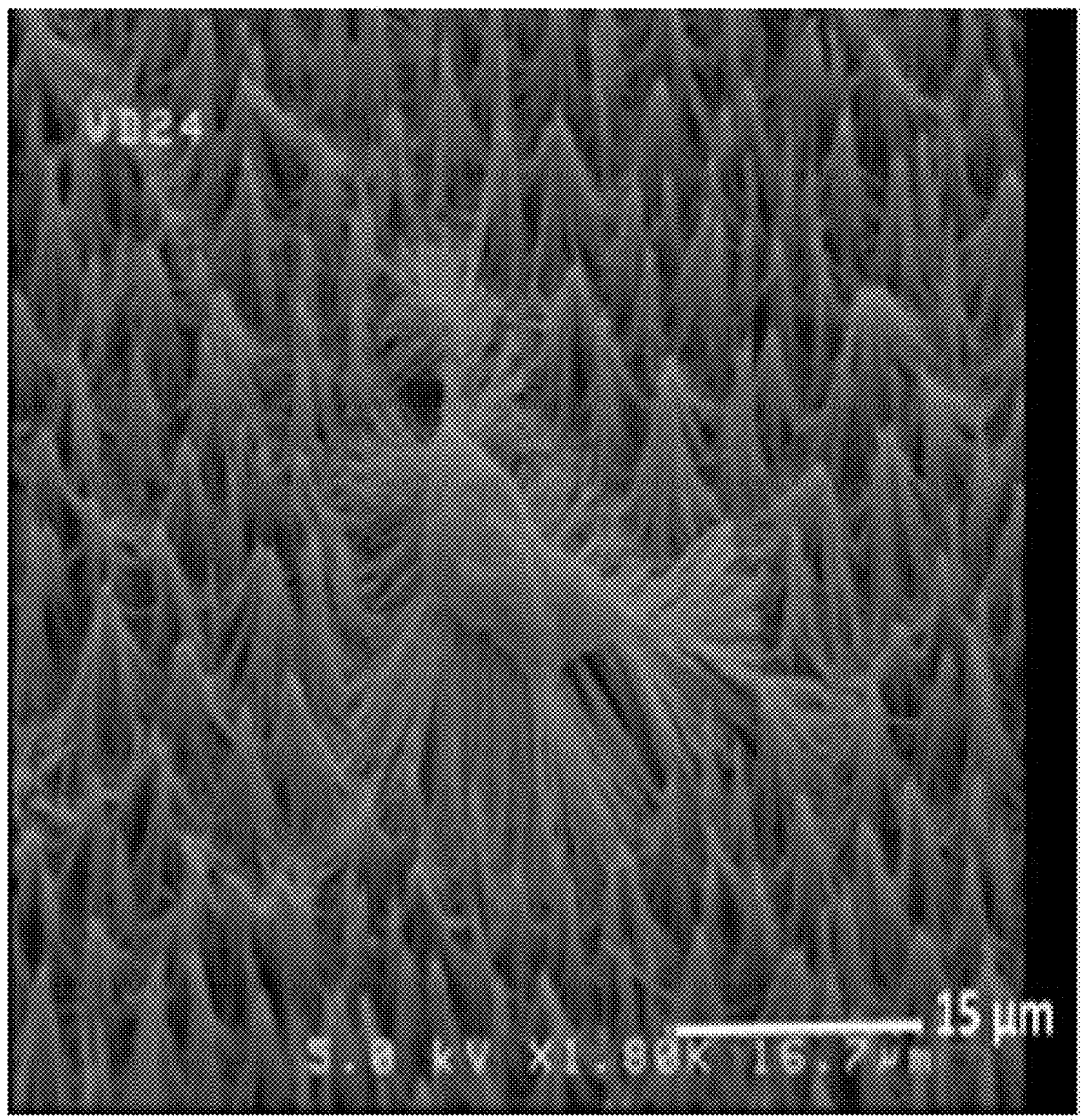
FIG. 14B shows a SEM image of the entrapment of several renal carcinoma cells on MWCNT arrays with large deflection angles of CNT beams from another side, according to an embodiment herein.

The entrapment of the renal carcinoma cells on the CNT arrays results in a deflection of the nanotube beams and these beam deflections are similar for each cancer cell. FIG. 14A and FIG. 14B show the SEM images of the entrapment of several renal carcinoma cells on the MWCNT arrays with large deflection angles of the CNT beams, according to an embodiment herein. With respect to FIG. 14A and FIG. 14B, the deformability of the cells deflected the CNTs. The deformability and the deflections of the cells from different sides are shown in the figures FIG. 14A and FIG. 14B.

Figure 15:
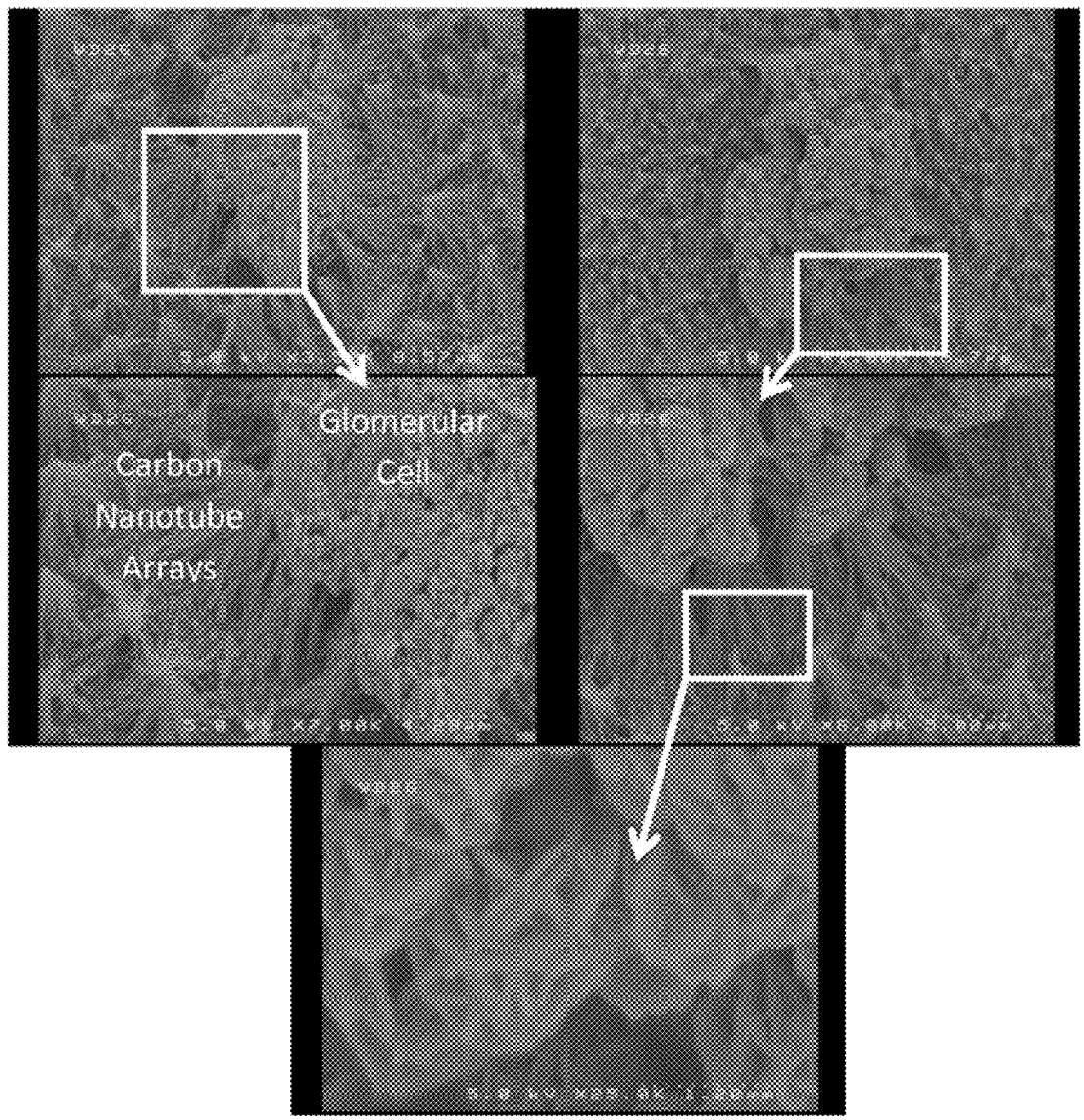
FIG. 15 shows a normal and enlarged views of a SEM image of glomerular cells onto CNTs arrays all over the surface, according to an embodiment herein.
Figure 16A:
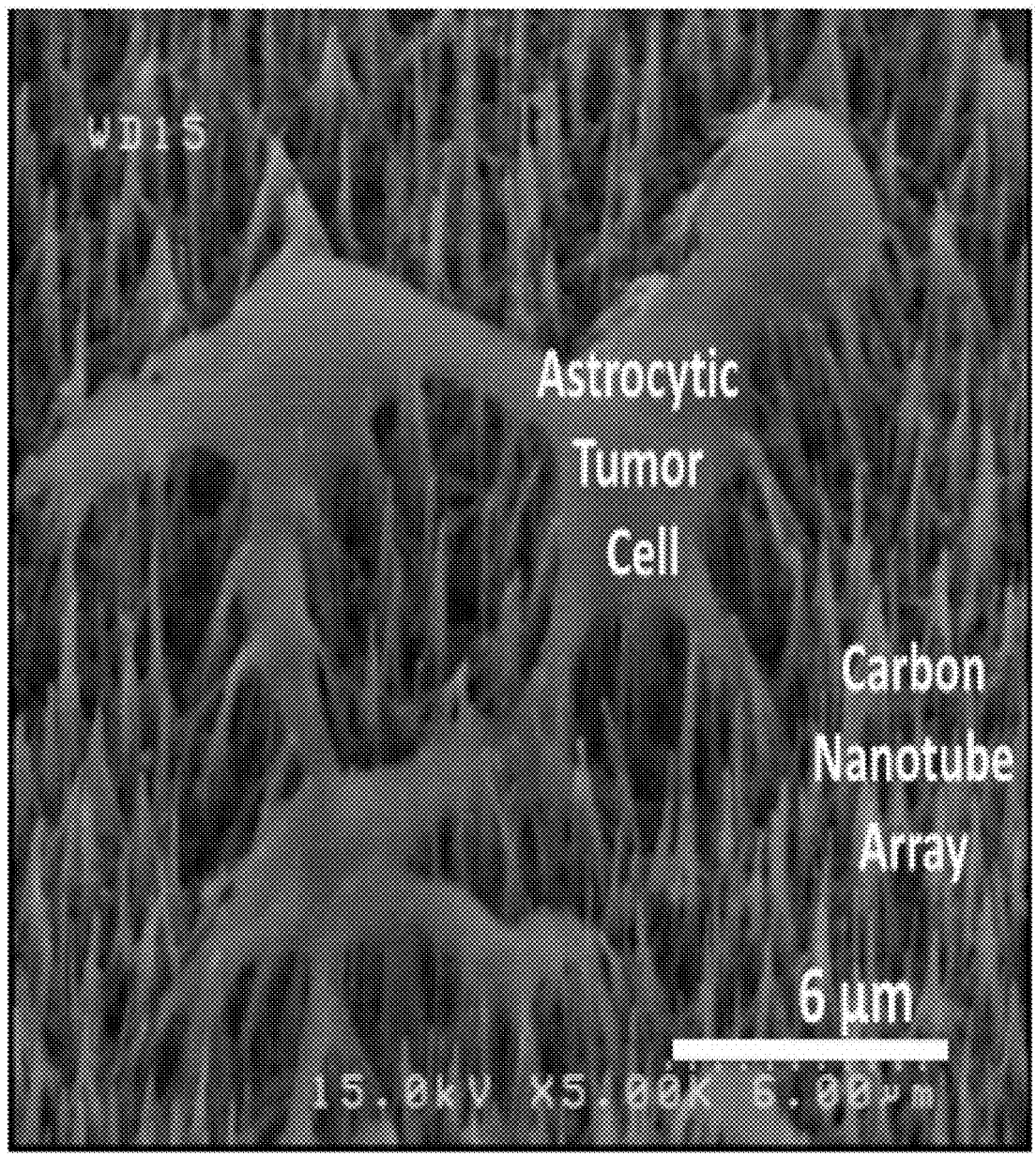
FIG. 16A shows a SEM micrograph of the Astrocytic tumor cells entrapment on MWCNT arrays at a scale of 6 μm, according to an embodiment herein.
Figure 16B:
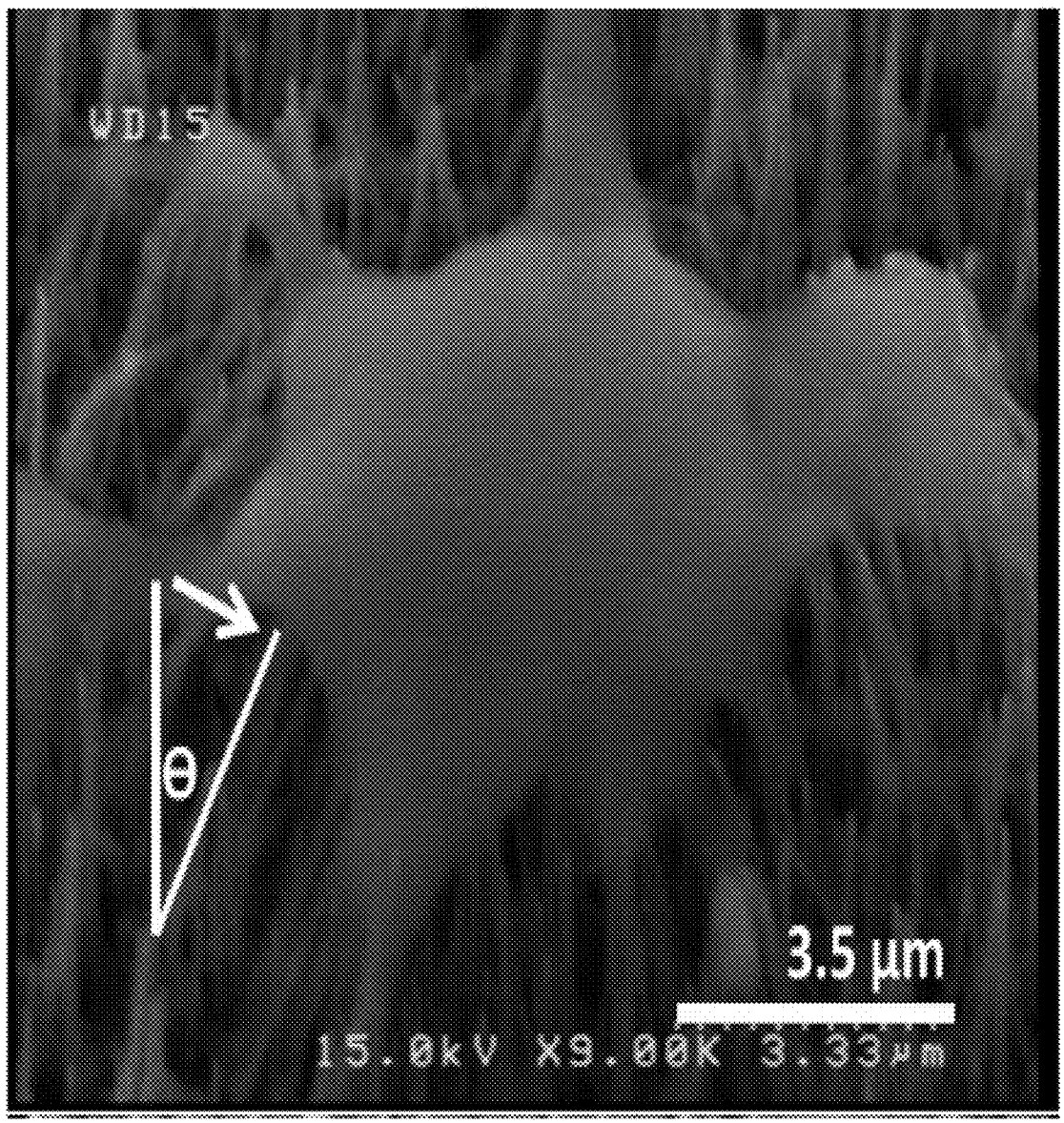
FIG. 16B shows an SEM micrograph of the Astrocytic tumor cells entrapment on MWCNT arrays indicating a deflection angle according to an embodiment herein.
Figure 16C:
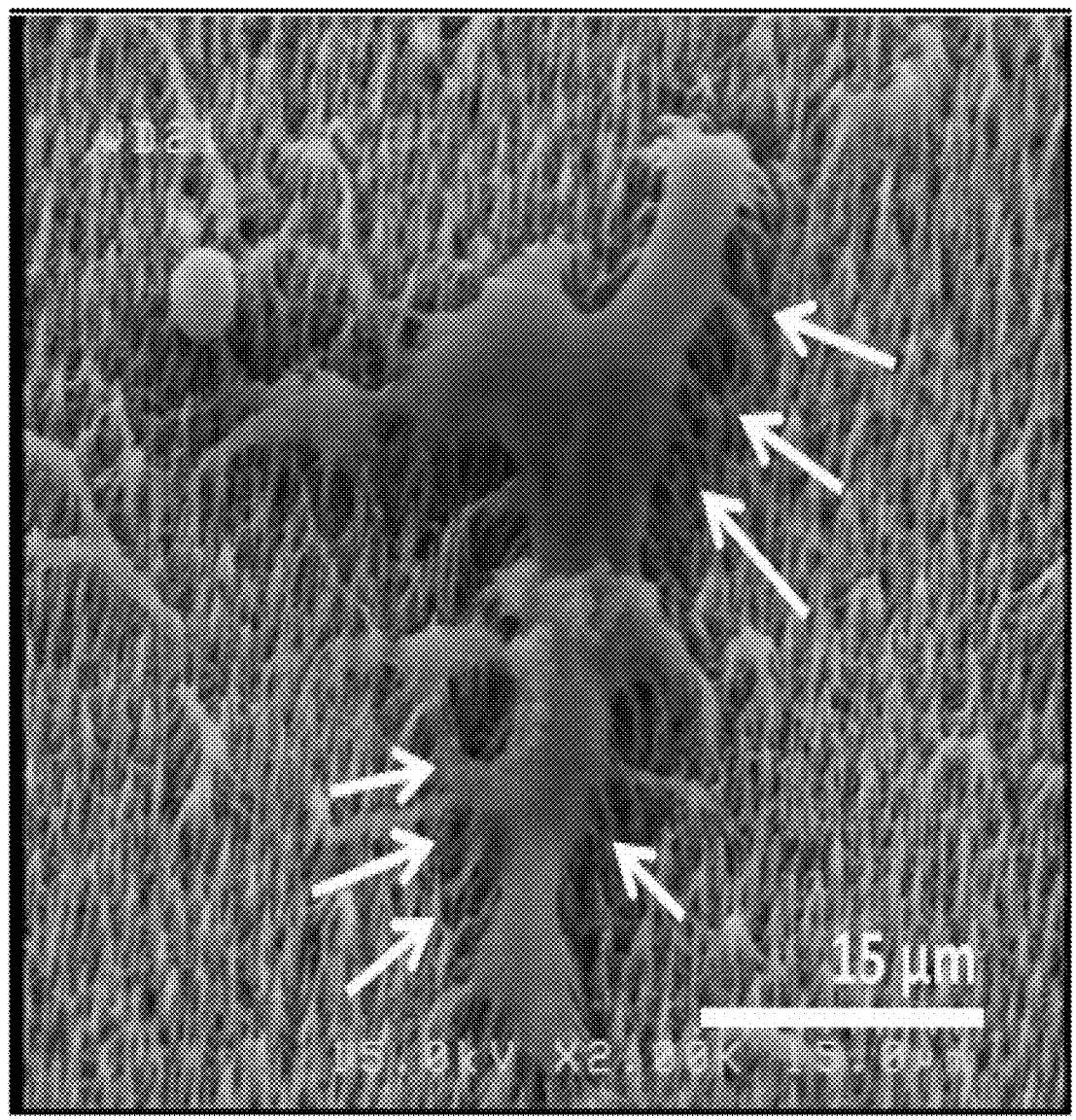
FIG. 16C shows an SEM micrograph of the Astrocytic tumor cells entrapment on MWCNT arrays indicating a direction of force, according to an embodiment herein.
Figure 16D:
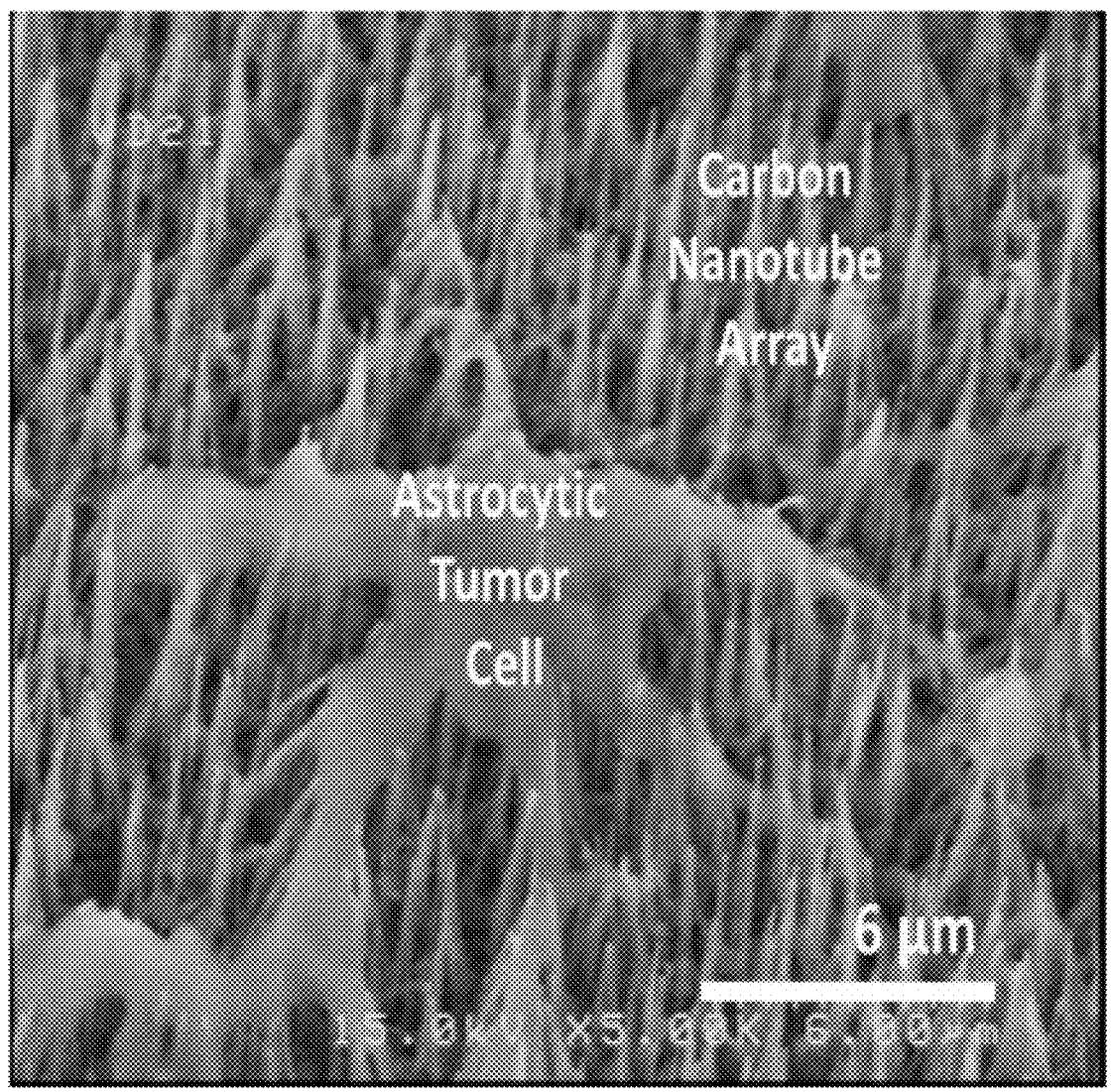
FIG. 16D shows an SEM micrograph of the Astrocytic tumor cells entrapment on MWCNT arrays at a scale of 6 μm, according to an embodiment herein.

Glomerular cells entrapment: It was observed that none of the renal benign cells were entrapped onto the CNTs except for a few glomerular cells as observed in FIG. 15. FIG. 15 show a SEM image of glomerular cells onto the CNTs arrays all over the surface, according to an embodiment herein. With respect to FIG. 15, it is also observed that these cells do not bend the CNTs inward as much as the malignant cells do. It is concluded that the softness of the malignant cells results in their entrapment and their deformation on nanotube arrays thereby bending the CNTs with a large deflection angle. On the other hand, the benign cells have more rigid cytoskeleton structures and because of their stiffness, they do not show a tendency to be entrapped and deformed upon an exposure to the CNTs. Thus the entrapment of glomerular cells is due to their porous surface structures, which agree well with the small deformation and deflection of the nanotubes as supported by the SEM micrographs shown in FIG. 15. Thus a less deflection is observed for glomerular cells, when compared with the malignant cells Entrapment of Astrocytic tumor cells on CNT arrays: It is interesting to observe that the same preparation process was applied for astrocytic tumor cells (a kind of brain tumor) which were obtained from a known case of astrocytoma and the same results were achieved for them also.

FIG. 16A-FIG. 16D show the SEM micrographs of the Astrocytic tumor cells entrapment on the MWCNT arrays at different magnification levels, according to an embodiment herein. With respect to FIG. 16A-FIG. 16D, the results obtained were same as that for the renal cells. Also the observed force direction and the deflection angle are same as that observed for the renal cancer cells. By observing such SEM images, one can extract a smaller angle of deflection for these cells as opposed to kidney ones. This is mainly due to the softness of brain tissues in comparison with that of the renal cells. The smaller deflection angles are observed due to a lower elasticity of the brain cells as compared to that of the renal cells. Consequently the CNT beams were deflected in much lower angles during the entrapment of Astrocytic tumor cells, when compared with that for the renal cells.

Estimation of cell elasticity and shear force: It has been found by Atomic Force Microscopy (AFM) indentation measurements that the elasticity of the healthy renal and brain tissues is about 7-10 kPa and 0.8-1 kPa respectively. In addition to the above, the metastatic tumor cells are softer than the benign cells by a value more than 80% thereby yielding an elasticity value of 1.5-2 kPa and 0.16-0.2 kPa for the renal carcinoma and Astrocytic tumor cells respectively. For conducting a research on these lines, AFM unit of Raster Scope DME Co. was employed to conduct an indentation measurement on the fixed RC (renal cancer) cells. The AFM data were analyzed by a Hertz model to obtain the values of the stiffness for such structures. The stiffness of the fixed RC cells was measured to be about 500 kPa's which agrees with the values given in the literature considering the effect of fixation on the cell elasticity.

Figure 17:
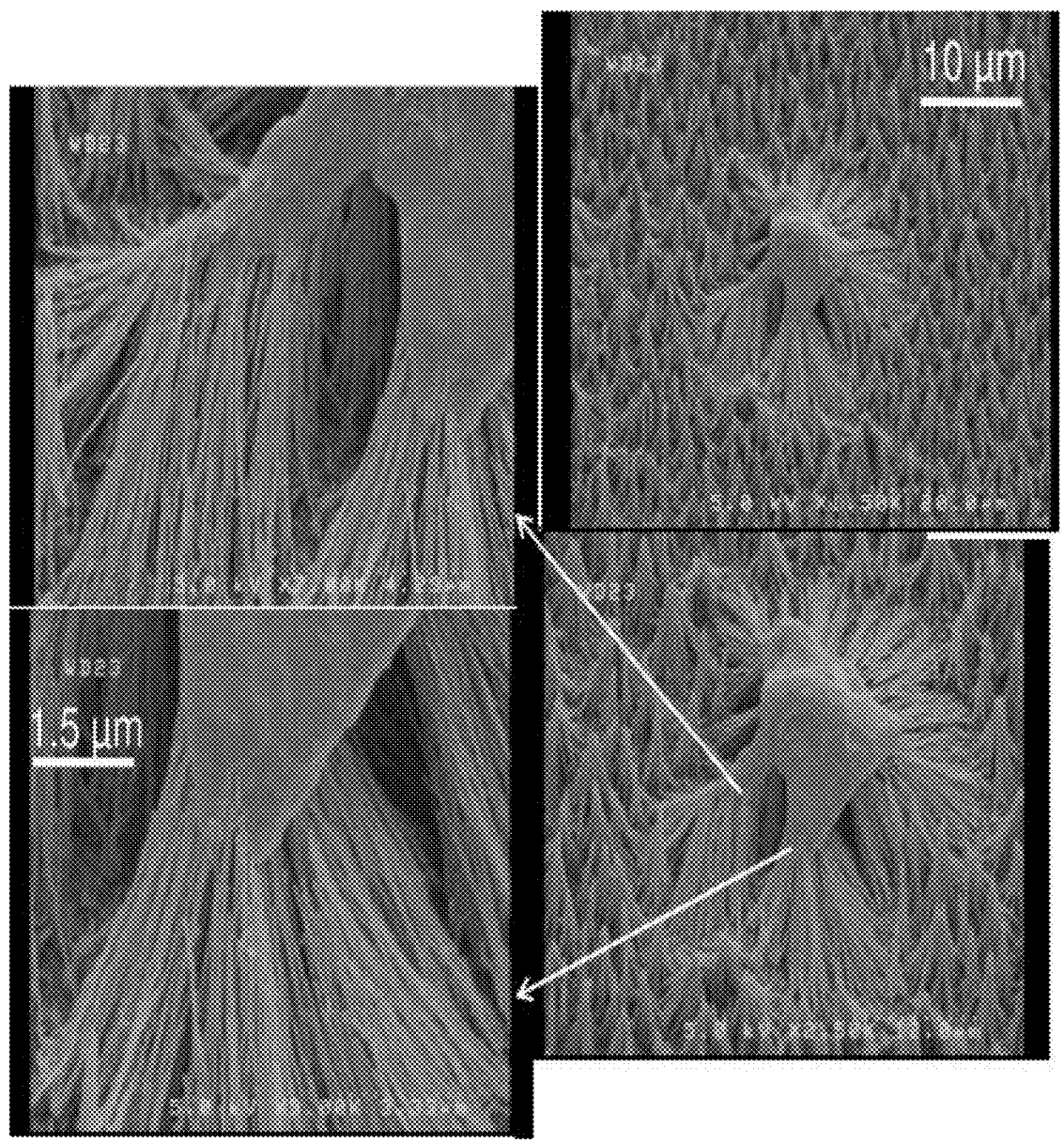
FIG. 17 shows a normal view and enlarged views of SEM images of CNT beam during deflection by the traction force applied by the Renal Carcinoma Cells, according to an embodiment herein.

It is deduced that the softness of the malignant cells leads to their entrapment and deformation on the nanotube arrays thereby bending the CNTs with a large deflection angle. On the other hand, the benign cells have more rigid cytoskeleton structures and because of their stiffness, they do not show a tendency to be entrapped and deformed upon exposure to the CNTs. The mechanical deformability, which is the main difference between the physical properties of the cancer cells and the healthy cells, resulted in the observed entrapment of cancer cells on the nanotube arrays. The shear-force applied by a single cell on the nanotube arrays could be derived by the large deflection methods. For this investigation, this method was applied to the renal cancer cells. The result of the force measurement indicates that the total force of a fixed RC-cell is approximately 0.3 nN while the force per unit surface of the substrate array is 0.5 pN/$\mu m^2$. Also the bending angle of the cell on the CNT array is about 37 degrees that is observable from the SEM micrograph shown in FIG. 10. In addition to the above, the force applied by a glomerular cell on the CNT array was calculated by a large deflection method and it was found to about 0.022 nN which is less than the force applied by a RC Cell. The interaction between cells and the CNTs which results in the deflection of the CNTs are illustrated and shown in FIG. 17. FIG. 17 shows a SEM image of the situation of CNTs beam during a deflection of the beam by the traction force applied by the Renal Carcinoma (RC) Cells, according to an embodiment herein. With respect to FIG. 17, the deformation of the cell after entrapment is also noticeable.

A similar experiment was also performed on the silicon black-surfaces where irregular nano-porous structures are present. No detectable selectivity is observed or found between the cancerous and healthy cells. This investigation is being pursued and more substantial findings will be presented elsewhere. This mechanism was repeated for the silicon micro rods and the silicon nano porous media. A selective cancer cell entrapment was observed on the silicon micro rods but the cells were stretched on the rigid rods. However no selective entrapment of the cells was observed on the silicon nano porous media.

Thus the changes in the mechanical properties of cancerous cells are used to detect the presence of cancerous cells in a tissue. The embodiments provided herein are used to diagnose the presence of cancer in biological tissues. The tissues include brain, colon and renal tissues.

The MWCNT vertically aligned arrays were used as suitable candidates for a cancer cell diagnosis. This detection is based on the difference in the fractions of entrapped cells on the CNT arrays which depends on the type and the metastatic stage of the cancerous cells. The entrapment of the cancer cells results in the deflection of the CNT beam. The deflection angle of CNT beam depends on the softness and deformability of the cancer cells and the type of its tissue. Our significant results are classified as follows:

The selective entrapment of cancer cells on vertically aligned MWCNT arrays depends on the deformability and elasticity of the cancer cells in comparison with that of the healthy ones. This is a novel method to detect the cancerous transformation of the cells.

The higher metastatic transformation of the cancer cells results in an observable increase in the cell entrapment levels on the CNT arrays which is believed to be because of the more deformable structure of higher metastatic cancer cells (HT 29 and SW 48 live cells).

The fixation of the cancer cells results in a sharp decrease of the entrapment of the cell on the CNT arrays because of the more rigid structure of the fixed cells.

A thermal irradiation of the CNT surface before a pumping of the cell solution on the substrate surface favorably affects the fraction of entrapped cells.

The rise in the flow rate of the cell solution pumped into CNT arrays results in a drop of the cell entrapment. An increase in the solution pumping flow rate from 2.5 cc/min to 20 cc/min results in a decrease in the fraction of cell entrapment by a factor of 15 (from 75% to 5%).

The entrapment mechanism of the cancer cells on the CNT arrays were investigated for both the cell line samples (colon cancer from two different stage of metastasis) and the clinical cells from the known cases of surgery (renal carcinoma and astrocytoma).

The healthy cells have the rigid and non-deformable structures in comparison with that of the cancer ones. No entrapment of the fixed healthy renal cells was occurred on the CNT arrays but the entrapment of fixed renal cancer cells on the CNT arrays was clearly observable. The shear force applied from the entrapped cells on the nanotube beams was approximately calculated to be 0.3 nN as opposed to healthy glomerular cells (0.022 nN).

The Astrocytoma cancer cells were entrapped on the CNT arrays and deflect the nanotube beams in the lower angles and which is believed to be due to the softness of the brain tissue and the shape of astrocytoma cells.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments.

It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

Although the embodiments herein are described with various specific embodiments, it will be obvious for a person skilled in the art to practice the invention with modifications. However, all such modifications are deemed to be within the scope of the claims.

It is also to be understood that the following claims are intended to cover all of the generic and specific features of the embodiments described herein and all the statements of the scope of the embodiments which as a matter of language might be said to fall there between.

What is claimed is:
1. A method for detecting cancer cells in a plurality of tissue cells using vertically aligned multiwall carbon nanotubes (MWCNT's) comprising the steps of:
    preparing a first solution of the plurality of tissue cells;
    fabricating a substrate, wherein the substrate is an array of vertically aligned multiwall carbon nanotubes (MWCNT's);
    irradiating the substrate with thermal irradiation;
    pouring the first solution of the plurality of tissue cells on the substrate after the irradiation of said substrate;
    allowing an entrapment of the plurality of tissue cells on the substrate;
    drying the substrate in an air environment after the entrapment of the plurality of tissue cells;
    observing the substrate after the drying step in a field emission scanning electron microscope; and
    detecting cancer cells in the plurality of tissue cells by observing a deflection of the vertically aligned multiwall carbon nanotubes (MWCNT's) in the substrate, wherein the deflection is caused by a stress applied by the entrapped cancer cells, wherein said deflection is measured as a deflection angle, and wherein said deflection depends on biomechanical properties of the cancer cells, wherein the biomechanical properties include softness, deformability, and elasticity of the cancer cells, and wherein the cancer cells that are detected are colon cancer cells, renal cancer cells or astrocytoma cells, and wherein the plurality of tissue cells is selected from a group consisting of cells taken from a colon, a kidney, and a brain.

2. The method according to claim 1, wherein the array of vertically aligned multiwall carbon nanotubes (MWCNT's) is fabricated using a direct-current plasma enhanced chemical vapor deposition technique.

3. The method according to claim 1, wherein the array of vertically aligned multiwall carbon nanotubes (MWCNT's) is held at an angle of 45 degrees during the pouring step.

4. The method according to claim 1, wherein the first solution of the plurality of tissue cells is poured on the substrate using a peristaltic pump.

5. The method according to claim 1, wherein the first solution of the plurality of tissue cells is poured on the substrate at a preset flow rate and wherein the preset flow rate is within a range of 2.5 cc/min-20 cc/min.

6. The method according to claim 1, wherein a field emission scanning electron microscope is used to detect the deflection of the vertically aligned multiwall carbon nanotubes (MWCNT's) due to the entrapment of colon cancer cells, wherein the colon cancer cells are selected from a group consisting of SW48 and HT29 colon cancer cell lines.

7. The method according to claim 1, wherein the cancer cells are detected based on the deflection angle of the carbon nanotubes which depends on the softness of the cancer cells and a plurality of healthy cells, wherein the softness of the cancer cells is more when compared to the softness of the healthy cells.

8. The method according to claim 1, wherein the cancer cells are detected based on the deflection angle of the carbon nanotubes which depends on the deformability and elasticity of the cancer cells and a plurality of healthy cells, wherein the deformability and elasticity of the cancer cells on the substrate is more when compared to the deformability and elasticity of the healthy cells.

9. The method according to claim 1, wherein the deflection angle of the vertically aligned multiwalled carbon nanotubes (MWCNT's) depends on the type of the tissue cells or cancer cells.

* * * * *